United States Patent
Díaz-Fernández et al.

(10) Patent No.: US 9,512,142 B2
(45) Date of Patent: Dec. 6, 2016

(54) TRICYCLIC TRIAZOLIC COMPOUNDS

(71) Applicant: LABORATORIOS DEL DR. ESTEVE S.A., Barcelona (ES)

(72) Inventors: José-Luís Díaz-Fernández, Manresa (ES); Carmen Almansa-Rosales, Barcelona (ES); Félix Cuevas-Cordobés, Valdemoro (ES)

(73) Assignee: LABORATORIOS DEL DR. ESTEVE S.A., Barcelona (ES)

( * ) Notice: Subject to any disclaimer, the term of this patent is extended or adjusted under 35 U.S.C. 154(b) by 0 days.

(21) Appl. No.: 14/785,128

(22) PCT Filed: Apr. 21, 2014

(86) PCT No.: PCT/EP2014/058036
§ 371 (c)(1),
(2) Date: Oct. 16, 2015

(87) PCT Pub. No.: WO2014/170494
PCT Pub. Date: Oct. 23, 2014

(65) Prior Publication Data
US 2016/0060275 A1    Mar. 3, 2016

(30) Foreign Application Priority Data
Apr. 19, 2013   (EP) .................................... 13382143

(51) Int. Cl.
*C07D 498/14* (2006.01)
*C07D 498/16* (2006.01)
(52) U.S. Cl.
CPC ........... *C07D 498/16* (2013.01); *C07D 498/14* (2013.01)

(58) Field of Classification Search
CPC ........................... C07D 498/14; C07D 498/16
USPC ....................................... 544/101; 514/230.2
See application file for complete search history.

(56) References Cited

FOREIGN PATENT DOCUMENTS

WO    WO 2009/071657    6/2009

OTHER PUBLICATIONS

Bowen, Pharmaceutica Acta Helvetiae, vol. 74, p. 211-218, 2000.
Dehaven-Hudkins, et al., European Journal of Pharmacology, Molecular Pharmacology Section, vol. 227, p. 371-378, 1992.
European Search Report With Written Opinion for EP13382143 of Jun. 26, 2013.
Hanner, et al., Proc. Natl. Acad. Sci. USA, vol. 93, p. 8072-8077, Jul. 1996.
International Search Report for PCT/EP2014/058036 ofMay 27, 2014.
Kaiser, Neurotransmissions, vol. 7, No. 1, p. 1-5, 1991.
Merskey, et al., Classification of Chronic Pain Second Edition, p. 210-213, 2002.
Oliva, et al., Organic Letters, vol. 10, No. 6, p. 1617-1619, 2008.
Quirionx, Tips, vol. 13, p. 85-86, Mar. 1982.
Ronsisvalle, et al., Pure Appl. Chem., vol. 73, No. 9, p. 1499-1509, 2001.
Schaus, et al., Journal Org. Chem. vol. 62, p. 4197-4199, 1997.
Snyder, et al., Journal of Neuropsychiatry, vol. 1, No. 1, p. 7-15, Winter 1998.
Tsuzuki, et al., Tetrahedron: Asymmetry, vol. 12, p. 2989-2997, 2001.
Walker, et al., Pharmacological Review., vol. 42, No. 4, p. 355-402, 1990.

*Primary Examiner* — Kahsay Habte
(74) *Attorney, Agent, or Firm* — Hueschen and Sage

(57) ABSTRACT

The present invention relates to new tricyclic triazolic compounds having a great affinity for sigma receptors, especially sigma-1 receptors, as well as to the process for the preparation thereof, to compositions comprising them, and to their use as medicaments.

15 Claims, No Drawings

TRICYCLIC TRIAZOLIC COMPOUNDS

FIELD OF THE INVENTION

The present invention relates to new tricyclic triazolic compounds having a great affinity for sigma receptors, especially sigma-1 receptors, as well as to the process for the preparation thereof, to compositions comprising them, and to their use as medicaments.

BACKGROUND OF THE INVENTION

The search for new therapeutic agents has been greatly aided in recent years by better understanding of the structure of proteins and other biomolecules associated with target diseases. One important class of these proteins are the sigma (σ) receptors, cell surface receptors of the central nervous system (CNS) which may be related to the dysphoric, hallucinogenic and cardiac stimulant effects of opioids. From studies of the biology and function of sigma receptors, evidence has been presented that sigma receptor ligands may be useful in the treatment of psychosis and movement disorders such as dystonia and tardive dyskinesia, and motor disturbances associated with Huntington's chorea or Tourette's syndrome and in Parkinson's disease (Walker, J. M. et al, Pharmacological Reviews, 1990, 42, 355). It has been reported that the known sigma receptor ligand rimcazole clinically shows effects in the treatment of psychosis (Snyder, S. H., Largent, B. L. J. Neuropsychiatry 1989, 1, 7). The sigma binding sites have preferential affinity for the dextrorotatory isomers of certain opiate benzomorphans, such as (+)SKF 10047, (+)cyclazocine, and (+)pentazocine and also for some narcoleptics such as haloperidol.

"The sigma receptor's" as used in this application is/are well known and defined using the following citation: This binding site represents a typical protein different from opioid, NMDA, dopaminergic, and other known neurotransmitter or hormone receptor families (G. Ronsisvalle et al. Pure Appl. Chem. 73, 1499-1509 (2001)).

The sigma receptor has at least two subtypes, which may be discriminated by stereoselective isomers of these pharmacoactive drugs. SKF 10047 has nanomolar affinity for the sigma 1 (σ-1) site, and has micromolar affinity for the sigma 2 (σ-2) site. Haloperidol has similar affinities for both subtypes.

The Sigma-1 receptor is a non-opiaceous type receptor expressed in numerous adult mammal tissues (e.g. central nervous system, ovary, testicle, placenta, adrenal gland, spleen, liver, kidney, gastrointestinal tract) as well as in embryo development from its earliest stages, and is apparently involved in a large number of physiological functions. Its high affinity for various pharmaceuticals has been described, such as for SKF-10047, (+)-pentazocine, haloperidol and rimcazole, among others, known ligands with analgesic, anxiolytic, antidepressive, antiamnesic, antipsychotic and neuroprotective activity. Sigma-1 receptor is of great interest in pharmacology in view of its possible physiological role in processes related to analgesia, anxiety, addiction, amnesia, depression, schizophrenia, stress, neuroprotection and psychosis [Kaiser et al (1991) Neurotransmissions 7 (1): 1-5], [Walker, J. M. et al, Pharmacological Reviews, 1990, 42, 355] and [Bowen W. D. (2000) Pharmaceutica Acta Helvetiae 74: 211-218].

The Sigma-2 receptor is also expressed in numerous adult mammal tissues (e.g. nervous system, immune system, endocrine system, liver, kidney). Sigma-2 receptors can be components in a new apoptosis route that may play an important role in regulating cell proliferation or in cell development. This route seems to consist of Sigma-2 receptors joined to intracellular membranes, located in organelles storing calcium, such as the endoplasmic reticulum and mitochondria, which also have the ability to release calcium from these organelles. The calcium signals can be used in the signaling route for normal cells and/or in induction of apoptosis.

Agonists of Sigma-2 receptors induce changes in cell morphology, apoptosis in several types of cell lines and regulate the expression of p-glycoprotein mRNA, so that they are potentially useful as antineoplasic agents for treatment of cancer. In fact, Sigma-2 receptor agonists have been observed to induce apoptosis in mammary tumour cell lines resistant to common antineoplasic agents that damage DNA. In addition, agonists of Sigma-2 receptors enhance the cytotoxic effects of these antineoplasic agents at concentrations in which the agonist is not cytotoxic.

Thus, agonists of Sigma-2 receptors can be used as antineoplasic agents at doses inducing apoptosis or at subtoxic doses in combination with other antineoplasic agents to revert the resistance to the drug, thereby allowing using lower doses of the antineoplasic agent and considerably reducing its adverse effects.

Antagonists of Sigma-2 receptors can prevent the irreversible motor side effects caused by typical neuroleptic agents. In fact, it has been found that antagonists of Sigma-2 receptors can be useful as agents for improving the weakening effects of delayed dyskinesia appearing in patients due to chronic treatment of psychosis with typical antipsychotic drugs, such as haloperidol. Sigma-2 receptors also seem to play a role in certain degenerative disorders in which blocking these receptors could be useful.

Endogenous sigma ligands are not known, although progesterone has been suggested to be one of them. Possible sigma-site-mediated drug effects include modulation of glutamate receptor function, neurotransmitter response, neuroprotection, behavior, and cognition (Quirion, R. et al. Trends Pharmacol. Sci., 1992, 13:85-86). Most studies have implied that sigma binding sites (receptors) are plasmalemmal elements of the signal transduction cascade. Drugs reported to be selective sigma ligands have been evaluated as antipsychotics (Hanner, M. et al. Proc. Natl. Acad. Sci., 1996, 93:8072-8077). The existence of sigma receptors in the CNS, immune and endocrine systems have suggested a likelihood that it may serve as link between the three systems.

In view of the potential therapeutic applications of agonists or antagonists of the sigma receptor, a great effort has been directed to find selective ligands. Thus, the prior art discloses different sigma receptor ligands.

For instance, the international patent application WO2007/098961 describes 4,5,6,7 tetrahydrobenzo[b]thiophene derivatives having pharmacological activity towards the sigma receptor.

Spiro[benzopyran] or spiro[benzofuran] derivatives were also disclosed in EP1847542 as well as pyrazole derivatives (EP1634873) with pharmacological activity on sigma receptors.

WO2009/071657 discloses compounds structurally related to the ones the current invention which moreover show activity towards sigma receptors. The compounds disclosed in this document do not show, however, sufficient solubility in physiological media so as to assure a proper bioavailability of the compound once administered to the patient.

Surprisingly, the authors of the present invention have observed that tricyclic triazolic compounds with general formula (I) not only show an affinity for Sigma receptor ranging from good to excellent, what makes them particularly suitable as pharmacologically active agents in medicaments for the prophylaxis and/or treatment of disorders or diseases related to Sigma receptors, but also they surprisingly have advantage of their high solubility in a physiological media. Solubility in aqueous media is of upper-most interest since it potentially affects the bioavailability of the drug. Solubility is, in some instances, directly affecting the dissolution rate of the drug, which may accelerate the uptake of the drug and may therefore act faster.

SUMMARY OF THE INVENTION

The present invention discloses novel compounds with great affinity to sigma receptors and having high solubility in a physiological media which might be used for the treatment of sigma related disorders or diseases.

Specifically, it is an object of the present invention novel tricyclic triazolic of general formula (I):

wherein
$R_1$ is selected from:
a —$(C(R_3)_2)_m$-aryl group in which the aryl group may be optionally substituted by at least one halogen atom;
a —$(C(R_3)_2)_m$-heteroaryl group in which the heteroaryl group may be optionally substituted by at least one substituent selected from a halogen, $C_{1-3}$-alkyl, $C_{1-3}$-alkoxy, $C_{1-3}$-haloalkoxy or $C_{1-3}$-haloalkyl and in which the heteroaryl group may optionally be condensed with an additional ring system;
a —$(C(R_3)_2)_n$-heterocycloalkyl group, in which the heterocycloalkyl group may be optionally substituted by at least one substituent selected from a halogen, $C_{1-3}$-alkyl, $C_{1-3}$-alkoxy, $C_{1-3}$-haloalkoxy or $C_{1-3}$-haloalkyl and contains at least one oxygen atom;
$R_2$ is selected from:
a phenyl group optionally substituted by at least one substituent selected from a halogen, $C_{1-3}$-alkoxy, $C_{1-3}$-haloalkoxy, $C_{1-3}$-haloalkyl or a hydroxyl group;
a heteroaryl group optionally substituted by at least one substituent selected from a halogen, $C_{1-3}$-alkyl $C_{1-3}$-alkoxy, $C_{1-3}$-haloalkoxy, $C_{1-3}$-haloalkyl or a hydroxyl group;
a heterocycloalkyl group being optionally substituted by at least one substituent selected from a halogen, $C_{1-3}$-alkyl, $C_{1-3}$-alkoxy, $C_{1-3}$-haloalcoxy, $C_{1-3}$-haloalkyl or a hydroxyl group;
$R_3$ is H or $C_{1-3}$ alkyl;
m is 1 to 3;
n is 0 to 3;
with the proviso that when $R_1$ is a —$(C(R_3)_2)_m$-aryl group, $R_2$ is not a phenyl group;
or a pharmaceutically acceptable salt, isomer, prodrug or solvate thereof.

It is also an object of the invention different processes for the preparation of compounds of formula (I).

Another object of the invention refers to the use of such compounds of general formula I for the treatment or prophylaxis of sigma receptor mediated diseases or conditions, especially sigma-1 mediated diseases or conditions. Within the group of diseases or conditions mediated by sigma receptor for which the compounds of the invention are effective diarrhea, lipoprotein disorders, hyperlipidemia, hypertriglyceridemia, hypercholesterolemia, obesity, migraine, arthritis, hypertension, arrhythmia, ulcer, glaucoma, learning, memory and attention deficits, cognition disorders, neurodegenerative diseases, demyelinating diseases, addiction to drugs and chemical substances including cocaine, amphetamine, ethanol and nicotine; tardive diskinesia, ischemic stroke, epilepsy, stroke, stress, cancer, psychotic conditions, in particular depression, anxiety or schizophrenia; inflammation or autoimmune diseases, may be cited. Compounds of the invention are especially useful in the treatment and prophylaxis of pain, especially neuropathic pain, inflammatory pain or other pain conditions involving allodynia and/or hyperalgesia.

It is also an object of the invention pharmaceutical compositions comprising one or more compounds of general formula (I) with at least one pharmaceutically acceptable excipient. The pharmaceutical compositions in accordance with the invention can be adapted in order to be administered by any route of administration, be it orally or parenterally, such as pulmonarily, nasally, rectally and/or intravenously. Therefore, the formulation in accordance with the invention may be adapted for topical or systemic application, particularly for dermal, subcutaneous, intramuscular, intra-articular, intraperitoneal, pulmonary, buccal, sublingual, nasal, percutaneous, vaginal, oral or parenteral application.

DETAILED DESCRIPTION OF THE INVENTION

The invention first relates to compounds of general formula (I)

wherein
$R_1$ is selected from:
a —$(C(R_3)_2)_m$-aryl group in which the aryl group may be optionally substituted by at least one halogen atom;
a —$(C(R_3)_2)_m$-heteroaryl group in which the heteroaryl group may be optionally substituted by at least one substituent selected from a halogen, $C_{1-3}$-alkyl, $C_{1-3}$-alkoxy, $C_{1-3}$-haloalcoxy or $C_{1-3}$-haloalkyl and in which the heteroaryl group may optionally be condensed with an additional ring system;
a —$(C(R_3)_2)_n$-heterocycloalkyl group, in which the heterocycloalkyl group may be optionally substituted by at least one substituent selected from a halogen, $C_{1-3}$-alkyl, $C_{1-3}$-alkoxy, $C_{1-3}$-haloalkoxy or $C_{1-3}$-haloalkyl and contains at least one oxygen atom;

R$_2$ is selected from:
a phenyl group optionally substituted by at least one substituent selected from a halogen, C$_{1-3}$-alkoxy, C$_{1-3}$-haloalkoxy, C$_{1-3}$-haloalkyl or a hydroxyl group;
a heteroaryl group optionally substituted by at least one substituent selected from a halogen, C$_{1-3}$-alkyl C$_{1-3}$-alkoxy, C$_{1-3}$-haloalkoxy, C$_{1-3}$-haloalkyl or a hydroxyl group;
a heterocycloalkyl group being optionally substituted by at least one substituent selected from a halogen, C$_{1-3}$-alkyl, C$_{1-3}$-alkoxy, C$_{1-3}$-haloalcoxy, C$_{1-3}$-haloalkyl or a hydroxyl group;
R$_3$ is H or C$_{1-3}$ alkyl;
m is 1 to 3;
n is 0 to 3;
with the proviso that when R$_1$ is a —(C(R$_3$)$_2$)$_m$-aryl group, R$_2$ is not a phenyl group;
or a pharmaceutically acceptable salt, isomer, prodrug or solvate thereof.

"Halogen" or "halo" as referred in the present invention represent fluorine, chlorine, bromine or iodine.

Alkyl radicals C$_{1-3}$, as referred to in the present invention, are saturated aliphatic radicals. They may be linear or branched and are optionally substituted. C$_{1-3}$-alkyl as expressed in the present invention means an alkyl radical of 1, 2 or 3 carbon atoms. Preferred alkyl radicals according to the present invention include but are not restricted to methyl, ethyl, propyl, n-propyl, isopropyl.

"Cycloalkyl" as referred to in the present invention, is understood as meaning saturated and unsaturated (but not aromatic), cyclic hydrocarbons having from 3 to 9 carbon atoms which can optionally be unsubstituted, mono- or polysubstituted. Examples for cycloalkyl radical preferably include but are not restricted to cyclopropyl, 2-methylcyclopropyl, cyclopropylmethyl, cyclobutyl, cyclopentyl, cyclopentylmethyl, cyclohexyl, cycloheptyl, cyclooctyl, adamantyl, noradamantyl. Cycloalkyl radicals, as defined in the present invention, are optionally mono- or polysubstituted by substitutents independently selected from a halogen, C$_{1-3}$-alkyl, C$_{1-3}$-alkoxy, C$_{1-3}$-haloalcoxy, C$_{1-3}$-haloalkyl or a hydroxyl group.

"Heterocycloalkyl" as referred to in the present invention, are understood as meaning saturated and unsaturated (but not aromatic), cyclic hydrocarbons having from 3 to 9 carbon atoms which can optionally be unsubstituted, mono- or polysubstituted and which have at least one heteroatom in their structure selected from N or O. Examples for heterocycloalkyl radical preferably include but are not restricted to pyrroline, pyrrolidine, pyrazoline, aziridine, azetidine, tetrahydropyrrole, oxirane, oxetane, dioxetane, tetrahydropyrane, tetrahydrofurane, dioxane, dioxolane, oxazolidine, piperidine, piperazine, morpholine, azepane or diazepane. Heterocycloalkyl radicals, as defined in the present invention, are optionally mono- or polysubstituted by substitutents independently selected from a halogen, C$_{1-3}$-alkyl, C$_{1-3}$-alkoxy, C$_{1-3}$-haloalkoxy, C$_{1-3}$-haloalkyl or a hydroxyl group.

"Aryl" as referred to in the present invention, is understood as meaning ring systems with at least one aromatic ring but without heteroatoms even in only one of the rings. These aryl radicals may optionally be mono- or polysubstituted by substitutents independently selected from a halogen, C$_{1-3}$-alkoxy, C$_{1-3}$-haloalcoxy, C$_{1-3}$-haloalkyl or a hydroxyl group. Preferred examples of aryl radicals include but are not restricted to phenyl, naphthyl, fluoranthenyl, fluorenyl, tetralinyl, indanyl or anthracenyl radicals, which may optionally be mono- or polysubstituted, if not defined otherwise.

"Heteroaryl" as referred to in the present invention, is understood as meaning heterocyclic ring systems which have at least one aromatic ring and may optionally contain one or more heteroatoms from the group consisting of nitrogen or oxygen and may optionally be mono- or polysubstituted by substitutents independently selected from a halogen, C$_{1-3}$-alkyl, C$_{1-3}$-alkoxy, C$_{1-3}$-haloalkoxy, C$_{1-3}$-haloalkyl or a hydroxyl group. Preferred examples of heteroaryls include but are not restricted to furan, benzofuran, pyrrole, pyridine, pyrimidine, pyridazine, pyrazine, quinoline, isoquinoline, phthalazine, triazole, pyrazole, isoxazole, indole, benzotriazole, benzodioxolane, benzodioxane, benzimidazole, carbazole and quinazoline.

The term "condensed" according to the present invention means that a ring or ring-system is attached to another ring or ring-system, whereby the terms "annulated" or "annelated" are also used by those skilled in the art to designate this kind of attachment.

The term "ring system" according to the present invention refers to ring systems comprising saturated, unsaturated or aromatic carbocyclic ring systems which contain optionally at least one heteroatom as ring member and which are optionally at least mono-substituted. Said ring systems may be condensed to other carbocyclic ring systems such as aryl groups, naphthyl groups, heteroaryl groups, cycloalkyl groups, etc.

The term "salt" is to be understood as meaning any form of the active compound according to the invention in which this assumes an ionic form or is charged and is coupled with a counter-ion (a cation or anion) or is in solution. By this are also to be understood complexes of the active compound with other molecules and ions, in particular complexes which are complexed via ionic interactions.

The term "physiologically acceptable salt" or "pharmaceutically acceptable salt" is understood in particular, in the context of this invention, as salt (as defined above) formed either with a physiologically tolerated acid, that is to say salts of the particular active compound with inorganic or organic acids which are physiologically tolerated—especially if used on humans and/or mammals—or with at least one, preferably inorganic, cation which are physiologically tolerated—especially if used on humans and/or mammals. Examples of physiologically tolerated salts of particular acids are salts of: hydrochloric acid, hydrobromic acid, sulfuric acid, hydrobromide, monohydrobromide, monohydrochloride or hydrochloride, methiodide, methanesulfonic acid, formic acid, acetic acid, oxalic acid, succinic acid, malic acid, tartaric acid, mandelic acid, fumaric acid, lactic acid, citric acid, glutamic acid, hippuric acid picric acid and/or aspartic acid. Examples of physiologically tolerated salts of particular bases are salts of alkali metals and alkaline earth metals and with NH$_4$.

The term "solvate" is to be understood as meaning any form of the active compound according to the invention in which this compound has attached to it via non-covalent binding another molecule (most likely a polar solvent) especially including hydrates and alcoholates, e.g. methanolate.

The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the compounds of the invention: esters, amino acid esters, phosphate esters, metal salts sulfonate esters, carbamates, and amides. Examples of well known methods of producing a prodrug of a given acting compound are known to those skilled in the art and can be found e.g. in Krogsgaard-Larsen et al. "Textbook of Drug design and Discovery" Taylor & Francis (April 2002).

Any compound that is a prodrug of a compound of formula (I) is within the scope of the invention. Particularly favored prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

In a particular and preferred embodiment of the invention $R_1$ is a benzyl optionally substituted by at least one halogen; a $-(C(R_3)_2)_m$-heteroaryl group in which the heteroaryl is a 5 or 6 membered heteroaryl radical containing from 1 to 3 heteroatoms selected from N or O and is optionally substituted by at least one substituent selected from a halogen, $C_{1-3}$-alkyl, $C_{1-3}$-alkoxy or $C_{1-3}$-haloalkyl; or a $-(C(R_3)_2)_n$-heterocycloalkyl group, in which the heterocycloalkyl group is a tetrahydropyranyl or as tetrahydrofuranyl group.

In a still more particular and preferred embodiment $R_1$ is selected from:

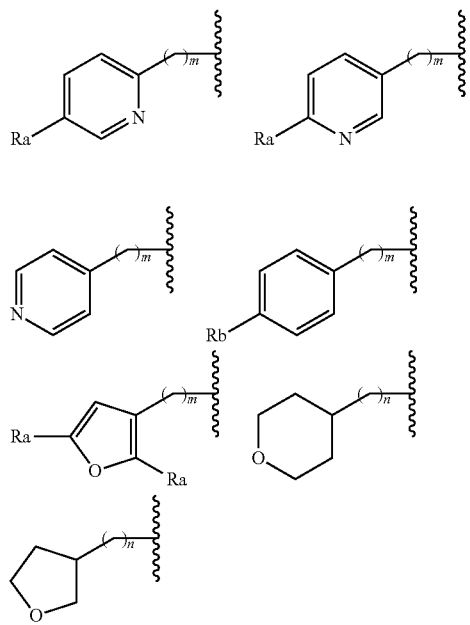

where $R_a$ represents a hydrogen, a halogen, $C_{1-3}$ alkyl, $C_{1-3}$-alkoxy or $C_{1-3}$ haloalkyl, $R_b$ represents a hydrogen or a halogen and m and n are as defined before for formula (I).

In another particular embodiment of the invention $R_2$ is a phenyl optionally substituted by at least one substituent selected from a halogen or $C_{1-3}$ haloalkyl; a 5 or 6 membered heteroaryl radical containing from 1 to 3 N atoms and optionally substituted by at least one substituent selected from a halogen, $C_{1-3}$-alkyl or $C_{1-3}$-alkoxy; or a tetrahydropyranyl group.

In a still more particular and preferred embodiment $R_2$ is selected from:

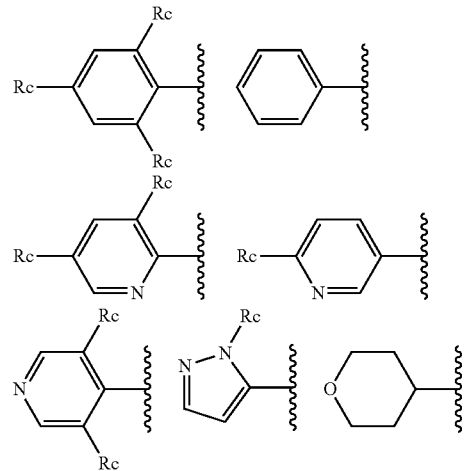

where $R_c$ represents a hydrogen, halogen, $C_{1-3}$ alkyl, $C_{1-3}$ alkoxy, $C_{1-3}$ haloalkyl.

The more preferred embodiment of the invention is that of compounds of general formula I where $R_1$ is selected from:

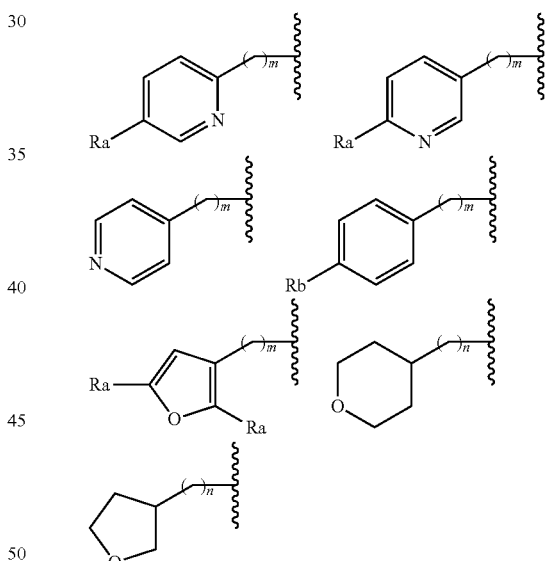

$R_2$ is selected from:

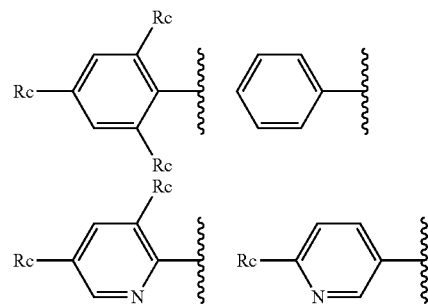

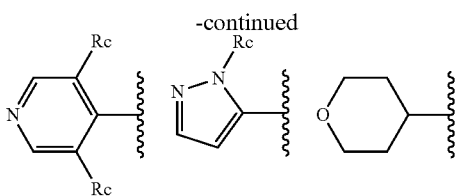

where $R_a$ represents a hydrogen, a halogen, $C_{1-3}$ alkyl, $C_{1-3}$-alkoxy or $C_{1-3}$ haloalkyl, $R_b$ represents a hydrogen or a halogen, $R_c$ represents a hydrogen, halogen, $C_{1-3}$ alkyl, $C_{1-3}$ alkoxy, $C_{1-3}$ haloalkyl and m and n are as defined before for formula (I).

Among all the compounds described in the general formula (I), particularly preferred are any of those compounds selected from:

(5aR,8aR)-3-(2-fluorophenyl)-7-(pyridin-3-ylmethyl)-4,5a,6,7,8,8a-hexahydropyrrolo[3,4-b][1,2,3]triazolo[1,5-d][1,4]oxazine hydrochloride (5aRS,8aRS)-3-(2-fluorophenyl)-7-(pyridin-4-ylmethyl)-4,5a,6,7,8,8a-hexahydropyrrolo[3,4-b][1,2,3]triazolo[1,5-d][1,4]oxazine hydrochloride (5aRS,8aRS)-3-(2-fluorophenyl)-7-(pyridin-2-ylmethyl)-4,5a,6,7,8,8a-hexahydropyrrolo[3,4-b][1,2,3]triazolo[1,5-d][1,4]oxazine hydrochloride (5aS,8aS)-3-(4-fluorophenyl)-7-(tetrahydro-2H-pyran-4-yl)-4,5a,6,7,8,8a-hexahydropyrrolo[3,4-b][1,2,3]triazolo[1,5-d][1,4]oxazine hydrochloride (5aR,8aR)-3-(4-fluorophenyl)-7-(tetrahydro-2H-pyran-4-yl)-4,5a,6,7,8,8a-hexahydropyrrolo[3,4-b][1,2,3]triazolo[1,5-d][1,4]oxazine hydrochloride (5aS,8aS)-3-(2-fluorophenyl)-7-(tetrahydro-2H-pyran-4-yl)-4,5a,6,7,8,8a-hexahydropyrrolo[3,4-b][1,2,3]triazolo[1,5-d][1,4]oxazine hydrochloride (5aR,8aR)-3-(2-fluorophenyl)-7-(tetrahydro-2H-pyran-4-yl)-4,5a,6,7,8,8a-hexahydropyrrolo[3,4-b][1,2,3]triazolo[1,5-d][1,4]oxazine hydrochloride (5aS,8aS)-3-(6-methoxypyridin-3-yl)-7-(tetrahydro-2H-pyran-4-yl)-4,5a,6,7,8,8a-hexahydropyrrolo[3,4-b][1,2,3]triazolo[1,5-d][1,4]oxazine hydrochloride (5aS,8aS)-3-(2-fluorophenyl)-7-((tetrahydro-2H-pyran-4-yl)methyl)-4,5a,6,7,8,8a-hexahydropyrrolo[3,4-b][1,2,3]triazolo[1,5-d][1,4]oxazine hydrochloride (5aR,8aR)-3-(2-fluorophenyl)-7-((tetrahydro-2H-pyran-4-yl)methyl)-4,5a,6,7,8,8a-hexahydropyrrolo[3,4-b][1,2,3]triazolo[1,5-d][1,4]oxazine hydrochloride (5aR,8aR)-3-(2-fluorophenyl)-7-((6-fluoropyridin-3-yl)methyl)-4,5a,6,7,8,8a-hexahydropyrrolo[3,4-b][1,2,3]triazolo[1,5-d][1,4]oxazine hydrochloride (5aR,8aR)-3-(2-fluorophenyl)-7-((6-methoxypyridin-3-yl)methyl)-4,5a,6,7,8,8a-hexahydropyrrolo[3,4-b][1,2,3]triazolo[1,5-d][1,4]oxazine hydrochloride (5aS,8aS)-3-(2-fluorophenyl)-7-((6-methoxypyridin-3-yl)methyl)-4,5a,6,7,8,8a-hexahydropyrrolo[3,4-b][1,2,3]triazolo[1,5-d][1,4]oxazine hydrochloride (5aR,8aR)-3-(2-fluorophenyl)-7-((6-(trifluoromethyl)pyridin-3-yl)methyl)-4,5a,6,7,8,8a-hexahydropyrrolo[3,4-b][1,2,3]triazolo[1,5-d][1,4]oxazine hydrochloride (5aS,8aS)-3-(2-fluorophenyl)-7-(((R)-tetrahydrofuran-3-yl)methyl)-4,5a,6,7,8,8a-hexahydropyrrolo[3,4-b][1,2,3]triazolo[1,5-d][1,4]oxazine hydrochloride (5aR,8aR)-3-(2-fluorophenyl)-7-(((S)-tetrahydrofuran-3-yl)methyl)-4,5a,6,7,8,8a-hexahydropyrrolo[3,4-b][1,2,3]triazolo[1,5-d][1,4]oxazine hydrochloride (5aS,8aS)-3-(2-fluorophenyl)-7-(((S)-tetrahydrofuran-3-yl)methyl)-4,5a,6,7,8,8a-hexahydropyrrolo[3,4-b][1,2,3]triazolo[1,5-d][1,4]oxazine hydrochloride (5aR,8aR)-3-(2-fluorophenyl)-7-(((R)-tetrahydrofuran-3-yl)methyl)-4,5a,6,7,8,8a-hexahydropyrrolo[3,4-b][1,2,3]triazolo[1,5-d][1,4]oxazine hydrochloride (5aR,8aR)-7-((6-ethoxypyridin-3-yl)methyl)-3-(2-fluorophenyl)-4,5a,6,7,8,8a-hexahydropyrrolo[3,4-b][1,2,3]triazolo[1,5-d][1,4]oxazine hydrochloride (5aS,8aS)-7-((6-ethoxypyridin-3-yl)methyl)-3-(2-fluorophenyl)-4,5a,6,7,8,8a-hexahydropyrrolo[3,4-b][1,2,3]triazolo[1,5-d][1,4]oxazine hydrochloride (5aRS,8aRS)-3-(4-fluorophenyl)-7-(furan-3-ylmethyl)-4,5a,6,7,8,8a-hexahydropyrrolo[3,4-b][1,2,3]triazolo[1,5-d][1,4]oxazine hydrochloride (5aS,8aS)-3-(2,4-difluorophenyl)-7-((2,5-dimethylfuran-3-yl)methyl)-4,5a,6,7,8,8a-hexahydropyrrolo[3,4-b][1,2,3]triazolo[1,5-d][1,4]oxazine hydrochloride (5aR,8aR)-3-(2,4-difluorophenyl)-7-((2,5-dimethylfuran-3-yl)methyl)-4,5a,6,7,8,8a-hexahydropyrrolo[3,4-b][1,2,3]triazolo[1,5-d][1,4]oxazine hydrochloride (5aR,8aR)-7-(4-fluorobenzyl)-3-(pyridin-2-yl)-4,5a,6,7,8,8a-hexahydropyrrolo[3,4-b][1,2,3]triazolo[1,5-d][1,4]oxazine hydrochloride (5aS,8aS)-7-(4-fluorobenzyl)-3-(pyridin-2-yl)-4,5a,6,7,8,8a-hexahydropyrrolo[3,4-b][1,2,3]triazolo[1,5-d][1,4]oxazine hydrochloride (5aRS,8aRS)-7-(4-fluorobenzyl)-3-(pyridin-4-yl)-4,5a,6,7,8,8a-hexahydropyrrolo[3,4-b][1,2,3]triazolo[1,5-d][1,4]oxazine hydrochloride (5aS,8aS)-3-(2,4-difluorophenyl)-7-(tetrahydro-2H-pyran-4-yl)-4,5a,6,7,8,8a-hexahydropyrrolo[3,4-b][1,2,3]triazolo[1,5-d][1,4]oxazine hydrochloride (5aR,8aR)-3-(2,4-difluorophenyl)-7-(tetrahydro-2H-pyran-4-yl)-4,5a,6,7,8,8a-hexahydropyrrolo[3,4-b][1,2,3]triazolo[1,5-d][1,4]oxazine hydrochloride (5aR,8aR)-7-(4-fluorobenzyl)-3-(3-fluoropyridin-2-yl)-4,5a,6,7,8,8a-hexahydropyrrolo[3,4-b][1,2,3]triazolo[1,5-d][1,4]oxazine hydrochloride (5aS,8aS)-3-(5-fluoropyridin-2-yl)-7-(tetrahydro-2H-pyran-4-yl)-4,5a,6,7,8,8a-hexahydropyrrolo[3,4-b][1,2,3]triazolo[1,5-d][1,4]oxazine hydrochloride (5aS,8aS)-3-(pyridin-2-yl)-7-(tetrahydro-2H-pyran-4-yl)-4,5a,6,7,8,8a-hexahydropyrrolo[3,4-b][1,2,3]triazolo[1,5-d][1,4]oxazine hydrochloride (5aR,8aR)-7-benzyl-3-(pyridin-2-yl)-4,5a,6,7,8,8a-hexahydropyrrolo[3,4-b][1,2,3]triazolo[1,5-d][1,4]oxazine hydrochloride (5aS,8aS)-7-benzyl-3-(pyridin-2-yl)-4,5a,6,7,8,8a-hexahydropyrrolo[3,4-b][1,2,3]triazolo[1,5-d][1,4]oxazine hydrochloride (5aS,8aS)-7-(4-fluorobenzyl)-3-(pyridin-3-yl)-4,5a,6,7,8,8a-hexahydropyrrolo[3,4-b][1,2,3]triazolo[1,5-d][1,4]oxazine hydrochloride (5aR,8aR)-7-(4-fluorobenzyl)-3-(pyridin-3-yl)-4,5a,6,7,8,8a-hexahydropyrrolo[3,4-b][1,2,3]triazolo[1,5-d][1,4]oxazine hydrochloride (5aR,8aR)-7-(4-fluorobenzyl)-3-(3-fluoropyridin-4-yl)-4,5a,6,7,8,8a-hexahydropyrrolo[3,4-b][1,2,3]triazolo[1,5-d][1,4]oxazine hydrochloride (5aS,8aS)-7-(4-fluorobenzyl)-3-(3-fluoropyridin-4-yl)-4,5a,6,7,8,8a-hexahydropyrrolo[3,4-b][1,2,3]triazolo[1,5-d][1,4]oxazine hydrochloride (5aS,8aS)-3-(2-chloro-4-fluorophenyl)-7-(tetrahydro-2H-pyran-4-yl)-4,5a,6,7,8,8a-hexahydropyrrolo[3,4-b][1,2,3]triazolo[1,5-d][1,4]oxazine hydrochloride (5aR,8aR)-3-(2-chloro-4-fluorophenyl)-7-((6-fluoropyridin-3-yl)methyl)-4,5a,6,7,8,8a-hexahydropyrrolo[3,4-b][1,2,3]triazolo[1,5-d][1,4]oxazine hydrochloride
(5aR,8aR)-3-(2,4-difluorophenyl)-7-(2-(tetrahydro-2H-pyran-4-yl)ethyl)-4,5a,6,7,8,8a-hexahydropyrrolo[3,4-b][1,2,3]triazolo[1,5-d][1,4]oxazine hydrochloride
(5aS,8aS)-3-(2,4-difluorophenyl)-7-(2-(tetrahydro-2H-pyran-4-yl)ethyl)-4,5a,6,7,8,8a-hexahydropyrrolo[3,4-b][1,2,3]triazolo[1,5-d][1,4]oxazine hydrochloride
(5aR,8aR)-3-(2-chloro-4-fluorophenyl)-7-((tetrahydro-2H-pyran-4-yl)methyl)-4,5a,6,7,8,8a-hexahydropyrrolo[3,4-b][1,2,3]triazolo[1,5-d][1,4]oxazine hydrochloride
(5aS,8aS)-3-(2-chloro-4-fluorophenyl)-7-((tetrahydro-2H-pyran-4-yl)methyl)-4,5a,6,7,8,8a-hexahydropyrrolo[3,4-b][1,2,3]triazolo[1,5-d][1,4]oxazine hydrochloride
(5aR,8aR)-3-(2,4-dichlorophenyl)-7-((tetrahydro-2H-pyran-4-yl)methyl)-4,5a,6,7,8,8a-hexahydropyrrolo[3,4-b][1,2,3]triazolo[1,5-d][1,4]oxazine hydrochloride
(5aS,8aS)-3-(2,4-dichlorophenyl)-7-((tetrahydro-2H-pyran-4-yl)methyl)-4,5a,6,7,8,8a-hexahydropyrrolo[3,4-b][1,2,3]triazolo[1,5-d][1,4]oxazine hydrochloride
(5aS,8aS)-3-(2,4-dichlorophenyl)-7-(tetrahydro-2H-pyran-4-yl)-4,5a,6,7,8,8a-hexahydropyrrolo[3,4-b][1,2,3]triazolo[1,5-d][1,4]oxazine hydrochloride
(5aR,8aR)-3-(2-chloro-4-fluorophenyl)-7-(2-(tetrahydro-2H-pyran-4-yl)ethyl)-4,5a,6,7,8,8a-hexahydropyrrolo[3,4-b][1,2,3]triazolo[1,5-d][1,4]oxazine hydrochloride
(5aS,8aS)-3-(2-chloro-4-fluorophenyl)-7-(2-(tetrahydro-2H-pyran-4-yl)ethyl)-4,5a,6,7,8,8a-hexahydropyrrolo[3,4-b][1,2,3]triazolo[1,5-d][1,4]oxazine hydrochloride
(5aR,8aR)-3-(2-chloro-4-fluorophenyl)-7-((6-methoxypyridin-3-yl)methyl)-4,5a,6,7,8,8a-hexahydropyrrolo[3,4-b][1,2,3]triazolo[1,5-d][1,4]oxazine hydrochloride
(5aS,8aS)-3-(2-chloro-4-fluorophenyl)-7-((6-methoxypyridin-3-yl)methyl)-4,5a,6,7,8,8a-hexahydropyrrolo[3,4-b][1,2,3]triazolo[1,5-d][1,4]oxazine hydrochloride
(5aR,8aR)-3-(2,4-difluorophenyl)-7-((6-methoxypyridin-3-yl)methyl)-4,5a,6,7,8,8a-hexahydropyrrolo[3,4-b][1,2,3]triazolo[1,5-d][1,4]oxazine hydrochloride
(5aS,8aS)-3-(2,4-difluorophenyl)-7-((6-methoxypyridin-3-yl)methyl)-4,5a,6,7,8,8a-hexahydropyrrolo[3,4-b][1,2,3]triazolo[1,5-d][1,4]oxazine hydrochloride
(5aS,8aS)-3-(2,4-dichlorophenyl)-7-(2-(tetrahydro-2H-pyran-4-yl)ethyl)-4,5a,6,7,8,8a-hexahydropyrrolo[3,4-b][1,2,3]triazolo[1,5-d][1,4]oxazine hydrochloride
(5aR,8aR)-3-(2,4-dichlorophenyl)-7-(2-(tetrahydro-2H-pyran-4-yl)ethyl)-4,5a,6,7,8,8a-hexahydropyrrolo[3,4-b][1,2,3]triazolo[1,5-d][1,4]oxazine hydrochloride
(5aS,8aS)-3-(2-chloro-4-(trifluoromethyl)phenyl)-7-(tetrahydro-2H-pyran-4-yl)-4,5a,6,7,8,8a-hexahydropyrrolo[3,4-b][1,2,3]triazolo[1,5-d][1,4]oxazine hydrochloride
(5aS,8aS)-3-(2,4-dichlorophenyl)-7-(((S)-tetrahydrofuran-3-yl)methyl)-4,5a,6,7,8,8a-hexahydropyrrolo[3,4-b][1,2,3]triazolo[1,5-d][1,4]oxazine hydrochloride
(5aR,8aR)-3-(2,4-dichlorophenyl)-7-(((R)-tetrahydrofuran-3-yl)methyl)-4,5a,6,7,8,8a-hexahydropyrrolo[3,4-b][1,2,3]triazolo[1,5-d][1,4]oxazine hydrochloride
(5aS,8aS)-3-(2,4-dichlorophenyl)-7-(((R)-tetrahydrofuran-3-yl)methyl)-4,5a,6,7,8,8a-hexahydropyrrolo[3,4-b][1,2,3]triazolo[1,5-d][1,4]oxazine hydrochloride
(5aR,8aR)-3-(2,4-dichlorophenyl)-7-(((S)-tetrahydrofuran-3-yl)methyl)-4,5a,6,7,8,8a-hexahydropyrrolo[3,4-b][1,2,3]triazolo[1,5-d][1,4]oxazine hydrochloride
(5aR,8aR)-3-(2,4-difluorophenyl)-7-((2-methylfuran-3-yl)methyl)-4,5a,6,7,8,8a-hexahydropyrrolo[3,4-b][1,2,3]triazolo[1,5-d][1,4]oxazine hydrochloride
(5aS,8aS)-3-(2,4-difluorophenyl)-7-((2-methylfuran-3-yl)methyl)-4,5a,6,7,8,8a-hexahydropyrrolo[3,4-b][1,2,3]triazolo[1,5-d][1,4]oxazine hydrochloride
(5aS,8aS)-3-(2,4-difluorophenyl)-7-(furan-3-ylmethyl)-4,5a,6,7,8,8a-hexahydropyrrolo[3,4-b][1,2,3]triazolo[1,5-d][1,4]oxazine hydrochloride
(5aR,8aR)-3-(2,4-difluorophenyl)-7-(furan-3-ylmethyl)-4,5a,6,7,8,8a-hexahydropyrrolo[3,4-b][1,2,3]triazolo[1,5-d][1,4]oxazine hydrochloride
(5aR,8aR)-7-(4-fluorobenzyl)-3-(tetrahydro-2H-pyran-4-yl)-4,5a,6,7,8,8a-hexahydropyrrolo[3,4-b][1,2,3]triazolo[1,5-d][1,4]oxazine hydrochloride
(5aS,8aS)-7-(4-fluorobenzyl)-3-(tetrahydro-2H-pyran-4-yl)-4,5a,6,7,8,8a-hexahydropyrrolo[3,4-b][1,2,3]triazolo[1,5-d][1,4]oxazine hydrochloride
(5aR,8aR)-7-(4-fluorobenzyl)-3-(1-methyl-1H-pyrazol-5-yl)-4,5a,6,7,8,8a-hexahydropyrrolo[3,4-b][1,2,3]triazolo[1,5-d][1,4]oxazine hydrochloride A specific embodiment of the invention is that in which the tricyclic triazolic compounds of the invention represent a compound with the general formula (Ia):

(Ia)

where $R_1'$ is selected from is selected from:
a —$(C(R_3)_2)_m$-aryl group in which the aryl group may be optionally substituted by at least one halogen atom;
a —$(C(R_3)_2)_m$-heteroaryl group in which the heteroaryl group may be optionally substituted by at least one substituent selected from a halogen, $C_{1-3}$-alkyl, $C_{1-3}$-alkoxy, $C_{1-3}$-haloalkoxy or $C_{1-3}$-haloalkyl and in which the heteroaryl group may optionally be condensed with an additional ring system;
a —$(C(R_3)_2)_n$-heterocycloalkyl group, in which the heterocycloalkyl group may be optionally substituted by at least one substituent selected from a halogen, $C_{1-3}$-alkyl, $C_{1-3}$-alkoxy, $C_{1-3}$-haloalkoxy or $C_{1-3}$-haloalkyl and contains at least one oxygen atom;
$R_2$ is selected from:
a phenyl group optionally substituted by at least one substituent selected from a halogen, $C_{1-3}$-alkoxy, $C_{1-3}$-haloalkoxy, $C_{1-3}$-haloalkyl or a hydroxyl group;
a heteroaryl group optionally substituted by at least one substituent selected from a halogen, $C_{1-3}$-alkyl $C_{1-3}$-alkoxy, $C_{1-3}$-haloalkoxy, $C_{1-3}$-haloalkyl or a hydroxyl group;
a heterocycloalkyl group being optionally substituted by at least one substituent selected from a halogen, $C_{1-3}$-alkyl, $C_{1-3}$-alkoxy, $C_{1-3}$-haloalcoxy, $C_{1-3}$-haloalkyl or a hydroxyl group;
$R_3$ is H or $C_{1-3}$ alkyl;
m is 1 to 2; and
n is 0 to 2;
with the proviso that when $R_1$ is a —$(C(R_3)_2)_m$-aryl group, $R_2$ is not a phenyl group; or a pharmaceutically acceptable salt, isomer, prodrug or solvate thereof.

In another aspect, the invention refers to the processes for obtaining the compounds of general formula (I). Several procedures have been developed for obtaining all the compound derivatives of the invention, herein the procedures will be explained below in methods A, B and C.

Method A

Method A represents the process for synthesizing compounds according to general formula (Ia) that is compounds of formula (I) where m and n represents at least 1.

In this sense, a process is described for the preparation of a compound of general formula (Ia):

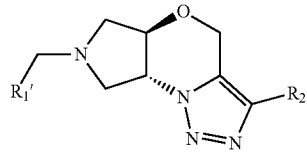
(Ia)

comprising the reaction between a compound of general formula (VI):

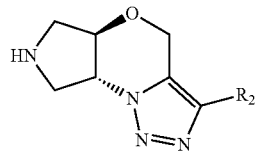
(VI)

with an aldehyde of general formula (VII):

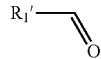
(VII)

where $R_2$ is as defined for formula (I) or (Ia) and $R_1'$ is as defined for formula (Ia).

The reductive amination reaction of compounds of formula (VI) and (VII) is preferably carried out in an aprotic solvent such as, for instance, dichloroethane and preferably in the presence of an organic base such as diisopropylethylamine and a reductive reagent such as sodium triacetoxyborohydride. The type of aldehyde to be used will depend on the meaning of the final substituent $R_1'$. All aldehydes (VII) used are commercially available.

In turn compound of general formula (VI) can be prepared by hydrolyzing a compound of general formula (V):

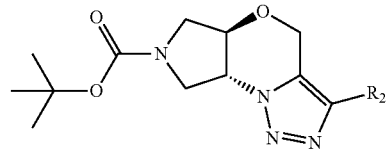
(V)

The hydrolyzation of compound (V) or its enatiomer or racemic is carried out in an acidic medium, preferably HCl and in an organic solvent such as, for instance, 1,4-dioxane.

Compound (V) is produced by heating a compound of general formula (IV):

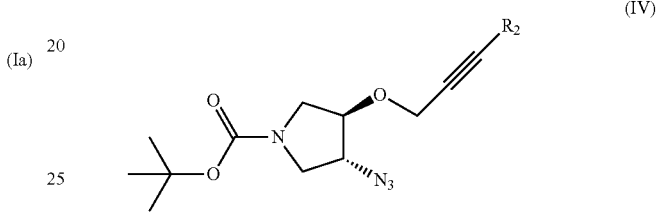
(IV)

or its enantiomer or racemic in xylene or toluene at a temperature range of 90-130° C.

Finally compound (IV) can be synthesized by the reaction of a compound of formula (II):

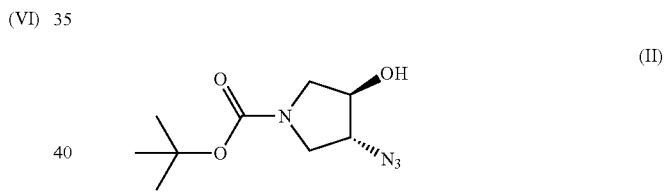
(II)

with a compound of general formula (III):

(III)

where X is a suitable leaving group such as a halogen or a sulfonate and $R_2$ is always as defined for compounds of formula (I) or (Ia).

The latter reaction is preferably carried out in an aprotic solvent such as tetrahydrofurane (THF) preferably in the presence of an inorganic base such as NaH and tetrabutylammonium iodide as catalyst at a temperature range of 0 PC to 30° C. Compound of formula (II) can be prepared enantiomerically pure or as racemic following methods reported in the literature (J. Org. Chem. 1997, 62, 4197-4199; Tetrahedron: Asymmetry 2001, 12, 2989-2997). Compounds of formula (III) can be prepared by conventional methods (Org. Lett. 2008, 10(8), 1617-1619).

The general synthetic route for preparing compound according to method A is represented in scheme 1:

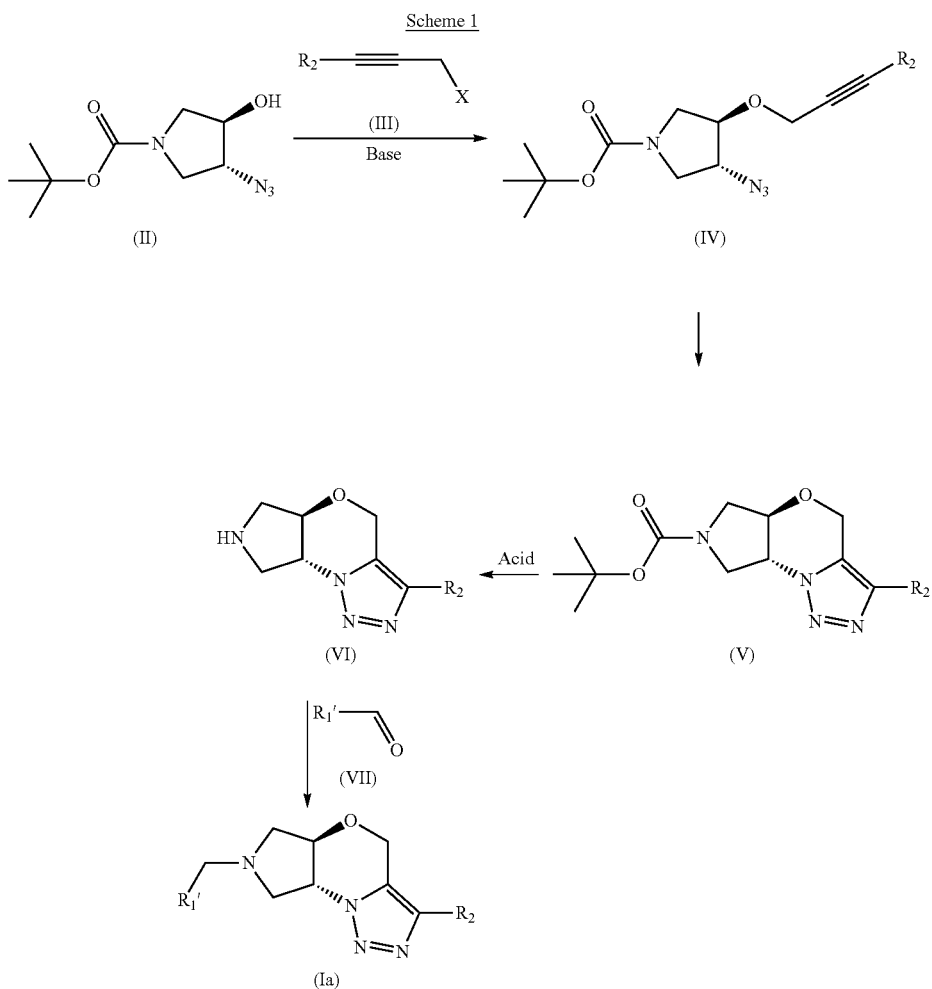

Alternatively, compound of general formula (IV) can also be prepared by reacting a compound of general formula (IVa) or its enantiomer or racemic:

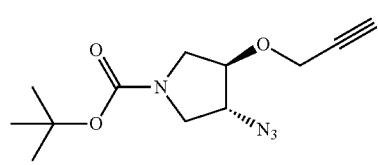

With a compound of general formula (X):

where Y is a suitable leaving group such as a halogen. This coupling reaction is preferably carried out in the presence of Pd(PPh$_3$)$_4$ and CuI as catalysts and triethylamine or mixture of triethylamine and DMF as solvent at a temperature range of 60-110° C. This reaction is represented in scheme 2:

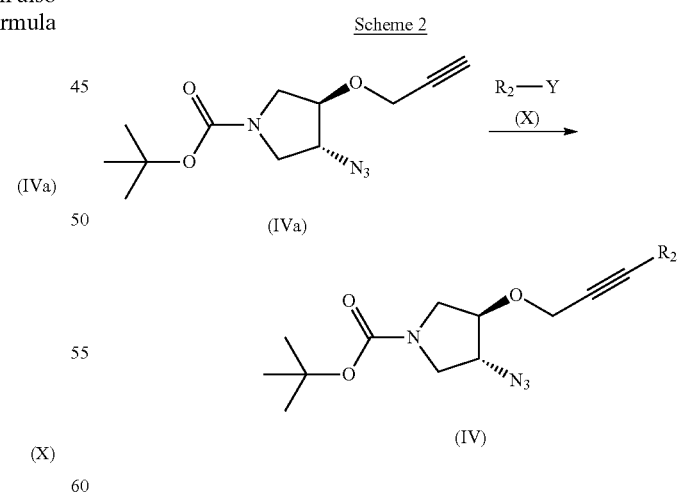

Intermediates of formula (V) can also be prepared in an alternative way a shown below in scheme 3. In addition, scheme 3 also represents the possibility of preparing compound of formula (V) where R$_2$ is a tetrahydropyrane as a particular embodiment (compound Va).

Scheme 3

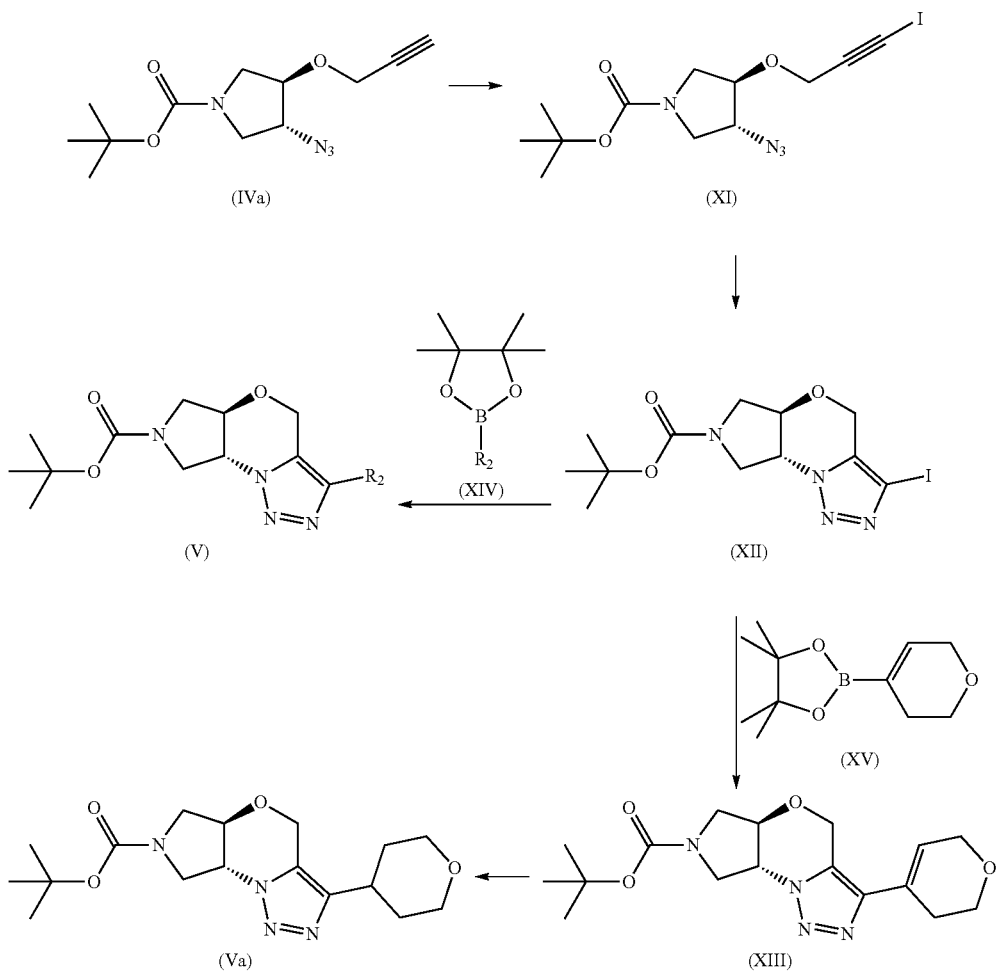

As shown above a compound of formula (IVa) or its enantiomer or racemic as prepared in the way shown is scheme 2 is subjected to iodination with a iodination reagent such as N-Iodomorpholine hydriodide preferably in the presence of CuI as catalyst and in a solvent such as THF, to give a compound of formula (XI). Compound (XI) is then heated in xylene or toluene at a temperature range of 90-130° C. to give compound (XII).

Compound of formula (XII) can be either reacted with a boronic pinacol ester of formula (XIV) to directly obtain a compound of general formula (V) or if a compound of general formula (Va) is desired a different route comprising the reaction of compound (XII) with a boronic pinacol ester of formula (XV) to obtain compound (XIII) is carried out. This reaction is carried out in the presence of Pd(PPh$_3$)$_4$ as catalyst and an inorganic base preferably K$_2$CO$_3$ or Na$_2$CO$_3$ in a mixture of organic solvents and water preferably a mixture of dimethoxyethane/ethanol/water or toluene/ethanol/water at a temperature range of 80-110° C. Alternatively, the reaction can be carried out in a microwave reactor. All boronic esters used are commercially available. As the final step for preparing compound of formula (Va), the alkenyl intermediate (XIII) or its enantiomer is reduced with ammonium formate preferably in the presence of Pd/C as catalyst in an organic solvent preferably a mixture of THF/methanol.

Method B

Method B represents an alternative way to method A for preparing compounds of general formula (Ia).

In this sense, a process is described for the preparation of a compound of general formula (Ia):

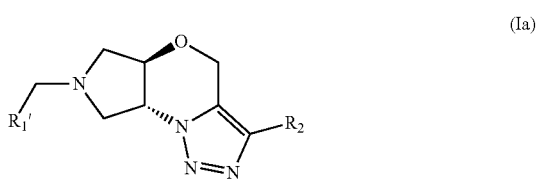

(Ia)

comprising the reduction of a compound of general formula (IX):

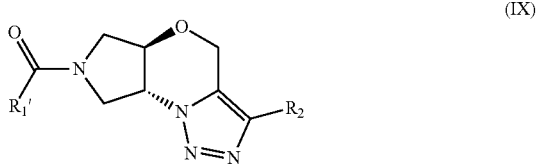

(IX)

The reduction of compound of general formula (IX) can be carried out with a reductive agent such as, for instance, BH$_3$ in an aprotic solvent preferably THF and preferably at a temperature range of 0° C. to 78° C.

In turn, compounds of general formula (IX) can be obtained by the reaction of a compound of general formula (VI) (as described in method A) with a compound of general formula (VIII):

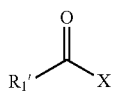

(VIII)

where X is a suitable leaving group such as a halogen. The latter reaction is preferably carried out in the presence of an organic base preferably diisopropylethylamine in an aprotic solvent preferably dichloromethane at a temperature range from 0° C. to 30° C. All compounds (VIII) used are commercially available.

The synthetic route of method B is represented in scheme 4 below:

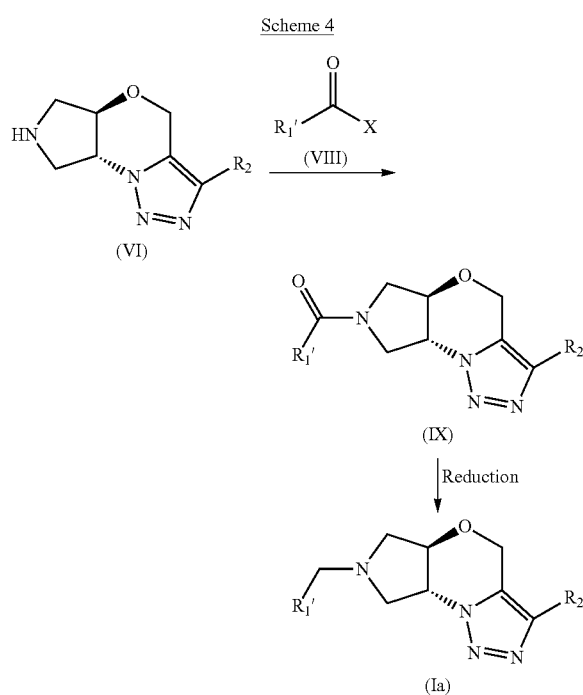

Method C

Method C represents the process for synthesizing compounds according to general formula (I) where n represents 0.

The process involves the reaction of a compound of formula (VI) with a ketone of formula (VIIa):

where R$_1$ represents a —C(R$_3$)$_2$)$_n$-heterocycloalkyl group being n=0

For instance, if a tetrahydro-2H-pyran-4-yl is desired in position R$_1$, the following ketone should be used:

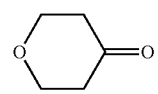

An additional aspect of the invention relates to the therapeutic use of the compounds of general formula (I). As mentioned above, compounds of general formula (I) show a strong affinity to sigma receptors and can behave as agonists, antagonists, inverse agonists, partial antagonists or partial agonists thereof. Therefore, compounds of general formula (I) are useful as medicaments.

They are suitable for the treatment and the prophylaxis of disorders and diseases mediated by sigma receptors, especially, sigma-1 receptors. In this sense, compounds of formula (I) are very good anxiolitic and immunosuppressant and are very useful in the treatment and prophylaxis of diarrhoea, lipoprotein disorders, hyperlipidemia, hypertriglyceridemia, hypercholesterolemia, obesity, migraine, arthritis, hypertension, arrhythmia, ulcer, glaucoma, learning, memory and attention deficits, cognition disorders, neurodegenerative diseases, demyelinating diseases, addiction to drugs and chemical substances including cocaine, amphetamine, ethanol and nicotine; tardive diskinesia, ischemic stroke, epilepsy, stroke, stress, cancer, psychotic conditions, in particular depression, anxiety or schizophrenia; inflammation or autoimmune diseases.

The compounds of formula (I) are especially suited for the treatment of pain, especially neuropathic pain, inflammatory pain or other pain conditions involving allodynia and/or hyperalgesia. PAIN is defined by the International Association for the Study of Pain (IASP) as "an unpleasant sensory and emotional experience associated with actual or potential tissue damage, or described in terms of such damage (IASP, Classification of chronic pain, 2nd Edition, IASP Press (2002), 210). Even though pain is always subjective its causes or syndromes can be classified.

In a preferred embodiment compounds of the invention are used for the treatment and prophylaxis of allodynia and more specifically mechanical or thermal allodynia.

In another preferred embodiment compounds of the invention are used for the treatment and prophylaxis of hyperalgesia.

In yet another preferred embodiment compounds of the invention are used for the treatment and prophylaxis of neuropathic pain and more specifically for the treatment and prophylaxis of hyperpathia.

A related aspect of the invention refers to the use of compounds of formula (I) for the manufacture of a medicament for the treatment of disorders and diseases mediated by sigma receptors, as explained before.

Another aspect of the invention is a pharmaceutical composition which comprises at least a compound of general formula (I) or a pharmaceutically acceptable salt, prodrug, isomer or solvate thereof, and at least a pharmaceutically acceptable carrier, additive, adjuvant or vehicle.

The pharmaceutical composition of the invention can be formulated as a medicament in different pharmaceutical forms comprising at least a compound binding to the sigma receptor and optionally at least one further active substance and/or optionally at least one auxiliary substance.

The auxiliary substances or additives can be selected among carriers, excipients, support materials, lubricants, fillers, solvents, diluents, colorants, flavour conditioners such as sugars, antioxidants and/or agglutinants. In the case of suppositories, this may imply waxes or fatty acid esters or preservatives, emulsifiers and/or carriers for parenteral application. The selection of these auxiliary materials and/or additives and the amounts to be used will depend on the form of application of the pharmaceutical composition.

The pharmaceutical composition in accordance with the invention can be adapted to any form of administration, be it orally or parenterally, for example pulmonarily, nasally, rectally and/or intravenously.

Preferably, the composition is suitable for oral or parenteral administration, more preferably for oral, intravenous, intraperitoneal, intramuscular, subcutaneous, intrathekal, rectal, transdermal, transmucosal or nasal administration.

The composition of the invention can be formulated for oral administration in any form preferably selected from the group consisting of tablets, dragees, capsules, pills, chewing gums, powders, drops, gels, juices, syrups, solutions and suspensions.

The composition of the present invention for oral administration may also be in the form of multiparticulates, preferably microparticles, microtablets, pellets or granules, optionally compressed into a tablet, filled into a capsule or suspended in a suitable liquid. Suitable liquids are known to those skilled in the art.

Suitable preparations for parenteral applications are solutions, suspensions, reconstitutable dry preparations or sprays.

The compounds of the invention can be formulated as deposits in dissolved form or in patches, for percutaneous application.

Skin applications include ointments, gels, creams, lotions, suspensions or emulsions.

The preferred form of rectal application is by means of suppositories.

The respective medicament may—depending on its route of administration—also contain one or more auxiliary substances known to those skilled in the art. The medicament according to the present invention may be produced according to standard procedures known to those skilled in the art.

The daily dosage for humans and animals may vary depending on factors that have their basis in the respective species or other factors, such as age, sex, weight or degree of illness and so forth. The daily dosage for humans may preferably be in the range from 1 to 2000, preferably 1 to 1500, more preferably 1 to 1000 milligrams of active substance to be administered during one or several intakes per day.

The following examples are merely illustrative of certain embodiments of the invention and cannot be considered as restricting it in any way.

EXAMPLES

Example of Preparation of and Intermediate of Formula (IV)

Synthesis of (3R,4R)-tert-butyl-3-azido-4-((3-(2-fluorophenyl)prop-2-yn-1-yl)oxy)-pyrrolidine-1-carboxylate

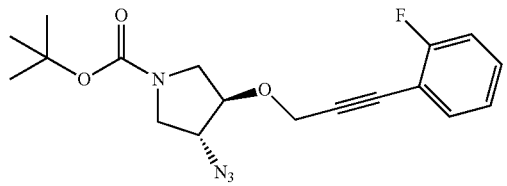 [SMILES: CC(C)(C)OC(=O)N1C[C@@H](N=[N+]=[N-])[C@H](OCC#Cc2ccccc2F)C1]

To a suspension of NaH (0.80 g, 60% dispersion in oil, 20 mmol) in dry THF (25 ml) cooled at 0° C. under nitrogen atmosphere, a solution of (3R,4R)-tert-butyl-3-azido-4-hydroxypyrrolidine-1-carboxylate (3.50 g, 15.3 mmol) in dry THF (25 ml) was slowly added. The reaction mixture was allowed to warm to room temperature and stirred for 45 min. Then, tetrabutylammonium iodide (TBAI) (0.57 g, 1.53 mmol) and a solution of 1-(3-bromoprop-1-ynyl)-2-fluorobenzene (3.92 g, 18.4 mmol) in THF (50 ml) were slowly added at 0° C. The reaction mixture was stirred from 0° C. to r.t. overnight. A saturated aqueous solution of $NH_4Cl$ was added and the mixture extracted with EtOAc. The organic layer was washed with water, dried over $Na_2SO_4$, filtered and concentrated under reduced pressure. The residue was purified by flash chromatography, silica gel, gradient hexane to ethyl acetate to give the titled compound (4.68 g, 85% yield) as yellow oil.

$^1$H-NMR (400 MHz, $CDCl_3$): mixture of two rotamers, δ ppm: 7.42 (m, 1H), 7.30 (m, 1H), 7.07 (m, 2H), 4.47 (m, 2H), 4.18 (m, 1H), 4.11 (m, 1H), 3.63 (m, 2H), 3.45 (m, 2H), 1.44 (s, 9H).

This method was used for the preparation of intermediates of formula (IV) in the synthesis of examples of formula (I) 1-21

Example of Preparation of an Intermediate of Formula (IV)

a) Synthesis of (3S,4S)-tert-butyl-3-azido-4-(prop-2-ynyloxy)pyrrolidine-1-carboxylate (S,S-IVa)

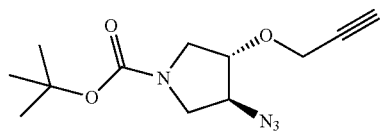 [SMILES: C#CCO[C@H]1CN(C(=O)OC(C)(C)C)C[C@@H]1N=[N+]=[N-]]

A solution of azido alcohol (3S,4S)-tert-butyl-3-azido-4-hydroxypyrrolidine-1-carboxylate (3.5 g, 15.3 mmol) in dry THF (28 ml) was added to a suspension of NaH (1.23 g, 60% dispersion in oil, 30.7 mmol) in THF (25 ml) under nitrogen, cooled at 0° C. When the bubbling was finished the reaction mixture was allowed to warm to room temperature and stirred for 45 min. Then, propargyl bromide (3.42 mL, 80% solution in toluene, 30.7 mmol) and a suspension of TBAI (0.57 g, 1.5 mmol) in THF (5 ml) were slowly added at 0° C. and the reaction was stirred overnight from 0° C. to rt. $NH_4Cl$ sat solution was added and extracted with EtOAc, washed with water, dried over $Na_2SO_4$, filtered and concentrated. Purification by flash chromatography, silica gel, gradient hexane to hexane:ethyl acetate (1:1) afforded the desired product (3.62 g, 89% yield) as yellow oil.

$^1$H-NMR (400 MHz, $CDCl_3$), mixture of two rotamers, δ ppm: 4.20 (m, 2H), 4.80 (m, 1H), 3.58 (m, 2H), 3.40 (m, 2H), 2.48 (s, 1H), 1.43 (s, 9H).

b) Synthesis of (3S,4S)-tert-butyl-3-azido-4-((3-(3-fluoropyridin-4-yl)prop-2-yn-1-yl)oxy)pyrrolidine-1-carboxylate

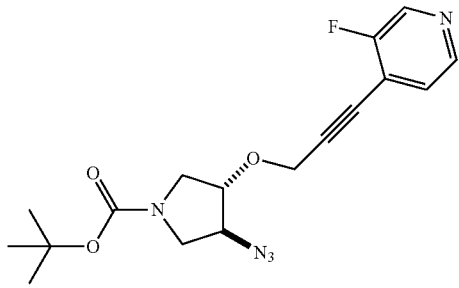 [SMILES: CC(C)(C)OC(=O)N1C[C@H](N=[N+]=[N-])[C@@H](OCC#Cc2ccncc2F)C1]

A mixture of CuI (20 mg, 0.10 mmol), Pd(PPh₃)₄ (24 mg, 0.021 mmol) and 3-fluoro-4-iodopyridine (469 mg, 2.10 mmol) in Et₃N (28 ml) under nitrogen was stirred at r.t. for 60 min. Then, a solution of (3S,4S)-tert-butyl-3-azido-4-(prop-2-ynyloxy)pyrrolidine-1-carboxylate (560 mg, 2.10 mmol) in Et₃N (17 ml) was added and the mixture was heated at 60° C. overnight. After cooling to r.t., water was added and the mixture was extracted with EtOAc. The organic phase was washed with brine, dried over Na₂SO₄, filtered and concentrated. Purification by flash chromatography, silica gel, gradient hexane to ethyl acetate, afforded the desired product (398 mg, 52%) and the corresponding cyclic intermediate of general formula (V) (118 mg, 15% yield).

¹H-NMR (400 MHz, CDCl₃): mixture of two rotamers, δ ppm: 8.50 (s, 1H), 8.39 (d, J=5 Hz, 1H), 7.33 (t, J=5 Hz, 1H), 4.50 (m, 2H), 4.15 (m, 1H), 4.10 (m, 1H), 3.65 (m, 2H), 3.47 (m, 2H), 1.46 (s, 9H).

This method was used for the preparation of intermediates of formula (IV) in the synthesis of examples of formula (I) 24-63.

Examples of Preparation of an Intermediate of Formula (V)

Synthesis of (5aR,8aR)-tert-butyl-3-(2-fluorophenyl)-5a,6,8,8a-tetrahydropyrrolo[3,4-b][1,2,3]triazolo[1,5-d][1,4]oxazine-7(4H)-carboxylate

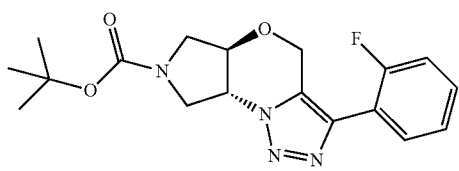 [SMILES: CC(C)(C)OC(=O)N1C[C@@H]2[C@@H](C1)OCc1c(-c3ccccc3F)nnn12]

A solution of (3R,4R)-tert-butyl-3-azido-4-((3-(2-fluorophenyl)prop-2-yn-1-yl)oxy)-pyrrolidine-1-carboxylate (4.68 g, 13.0 mmol) in xylene (560 ml) was heated at 120° C. overnight. The reaction mixture was cooled and the solvent evaporated. Purification by flash chromatography, silica gel, gradient hexane to ethyl acetate afforded the desired product (4.02 g, 86% yield) as a yellowish solid.

¹H-NMR (400 MHz, CDCl₃): mixture of two rotamers, δ ppm: 7.97 (m, 1H), 7.38 (m, 1H), 7.27 (td, J=8, 1 Hz, 1H), 7.14 (t, J=9 Hz, 1H), 5.33 (dd, J=16, 2 Hz, 1H), 5.15 (d, J=16 Hz, 1H), 4.6-4.2 (m, 2H), 4.1-3.8 (m, 2H), 3.59 (m, 1H), 3.39 (m, 1H), 1.50 (s, 9H).

Examples of Preparation of Intermediates of Formula (V)

a) Synthesis of (3R,4R)-tert-butyl-3-azido-4-((3-iodoprop-2-yn-1-yl)oxy)-pyrrolidine-1-carboxylate

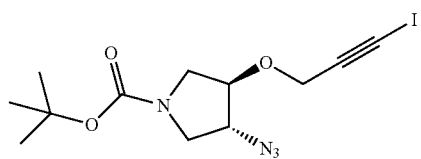 [SMILES: CC(C)(C)OC(=O)N1C[C@@H](N=[N+]=[N-])[C@H](OCC#CI)C1]

To a solution of (3R,4R)-tert-butyl-3-azido-4-(prop-2-ynyloxy)pyrrolidine-1-carboxylate (0.69 g, 2.6 mol) in THF (15 ml), CuI (25 mg, 0.13 mmol) and N-iodomorpholine hydriodide (1.0 g, 2.9 mmol) were added. The reaction mixture was stirred at r.t. for 2 h, after which a precipitate had formed. The suspension was poured onto a pad of neutral alumina and the filtrate was collected under vacuum. The solid phase was washed with DCM and the combined filtrate was concentrated by evaporation. The product was obtained as yellow oil (0.99 g, 97% yield).

¹H-NMR (400 MHz, CDCl₃): mixture of two rotamers, δ ppm: 4.38 (m, 2H), 4.07 (m, 1H), 4.03 (m, 1H), 3.61 (m, 2H), 3.44 (m, 2H), 1.46 (s, 9H).

b) Synthesis of (5aR,8aR)-tert-butyl-3-iodo-5a,6,8,8a-tetrahydropyrrolo[3,4-b][1,2,3]triazolo[1,5-d][1,4]oxazine-7(4H)-carboxylate

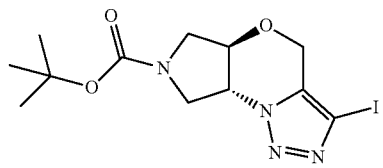 [SMILES: CC(C)(C)OC(=O)N1C[C@@H]2[C@@H](C1)OCc1c(I)nnn12]

A solution of (3R,4R)-tert-butyl-3-azido-4-((3-iodoprop-2-yn-1-yl)oxy)pyrrolidine-1-carboxylate (0.99 g, 2.5 mmol) in toluene (65 ml) was heated at 100° C. overnight. The reaction mixture was cooled and the solvent evaporated. Purification by flash chromatography, silica gel, gradient hexane to hexane:ethyl acetate (8:2) afforded the desired product (0.76 g, 77% yield). ¹H-NMR (400 MHz, CDCl₃), mixture of two rotamers, δ ppm: 5.11 (d, J=16 Hz, 1H), 4.92 (d, J=16 Hz, 1H), 4.5-4.2 (m, 2H), 4.0-3.8 (m, 2H), 3.51 (m, 1H), 3.37 (m, 1H), 1.49 (s, 9H).

c) Synthesis of (5aR,8aR)-tert-butyl-3-(3,6-dihydro-2H-pyran-4-yl)-5a,6,8,8a-tetrahydropyrrolo[3,4-b][1,2,3]triazolo[1,5-d][1,4]oxazine-7(4H)-carboxylate (XIII)

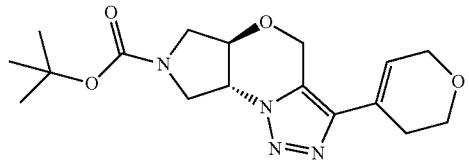 [SMILES: CC(C)(C)OC(=O)N1C[C@@H]2[C@@H](C1)OCc1c(C3=CCOCC3)nnn12]

To a mixture of (5aR,8aR)-tert-butyl-3-iodo-5a,6,8,8a-tetrahydropyrrolo[3,4-b][1,2,3]-triazolo[1,5-d][1,4]oxazine-7(4H)-carboxylate (250 mg, 0.64 mmol), 3,6-dihydro-2H-pyran-4-boronic acid pinacol ester (161 mg, 0.76 mol), $K_2CO_3$ (352 mg, 2.55 mmol) and Pd(Ph$_3$)$_4$ (37 mg, 0.032 mmol) under nitrogen, a mixture of Dimethoxyethane/EtOH/water 4/1/0.2 (21 ml) was added. The reaction mixture was heated at 90° C. overnight. The reaction mixture was cooled down, diluted with DCM, washed with sat. NaHCO$_3$ solution, dried over Na$_2$SO$_4$, filtered and concentrated under vacuum. Purification by flash chromatography, silica gel, gradient hexane to hexane:ethyl acetate (1:1) afforded the desired product (160 mg, 72% yield).

$^1$H-NMR (400 MHz, CDCl$_3$), mixture of two rotamers, δ ppm: 5.85 (s, 1H), 5.28 (d, J=16 Hz, 1H), 5.08 (d, J=16 Hz, 1H), 4.5-4.2 (m, 4H), 4.0-3.8 (m, 4H), 3.53 (m, 1H), 3.37 (m, 1H), 2.68 (m, 2H), 1.49 (s, 9H).

d) Synthesis of (5aR,8aR)-tert-butyl-3-(tetrahydro-2H-pyran-4-yl)-5a,6,8,8a-tetrahydropyrrolo[3,4-b][1,2,3]triazolo[1,5-d][1,4]oxazine-7(4H)-carboxylate (Va)

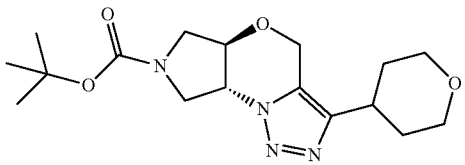 [SMILES: CC(C)(C)OC(=O)N1C[C@@H]2[C@@H](C1)OCc1c(C3CCOCC3)nnn12]

A suspension of (5aR,8aR)-tert-butyl-3-(3,6-dihydro-2H-pyran-4-yl)-5a,6,8,8a-tetrahydropyrrolo[3,4-b][1,2,3]triazolo[1,5-d][1,4]oxazine-7(4H)-carboxylate (325 mg, 0.93 mmol), ammonium formate (882 mg, 14.0 mmol) and Pd/C (20% w/w, 65 mg) in MeOH/THF (1:1) (30 ml) under nitrogen atmosphere was heated at 75° C. overnight. The suspension was filtered through celite and washed with MeOH. The filtrate was evaporated under vacuum and the residue obtained was portioned with DCM and water. The organic layer was washed with sat. NaHCO$_3$, dried over Na$_2$SO$_4$, filtered and the solvent removed under vacuum. The desired product was obtained as a white solid (319 mg, 98% yield).

$^1$H-NMR (400 MHz, CDCl$_3$), mixture of two rotamers, δ ppm: 5.24 (d, J=16 Hz, 1H), 5.02 (d, J=16 Hz, 1H), 4.5-4.2 (m, 2H), 4.06 (m, 2H), 4.0-3.8 (m, 2H), 3.53 (m, 3H), 3.36 (m, 1H), 3.00 (m, 1H), 1.85 (m, 4H), 1.49 (s, 9H).

e) Synthesis of (5aR,8aR)-7-(4-fluorobenzyl)-3-(1-methyl-1H-pyrazol-5-yl)-4,5a,6,7,8,8a-hexahydropyrrolo[3,4-b][1,2,3]triazolo[1,5-d][1,4]oxazine

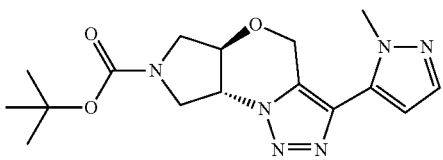 [SMILES: Cn1nccc1-c1nnn2c1CO[C@@H]1CN(C(=O)OC(C)(C)C)C[C@H]12]

A 25 mL microwave vial was charged with (5aR,8aR)-tert-butyl 3-iodo-5a,6,8,8a-tetrahydropyrrolo[3,4-b][1,2,3]triazolo[1,5-d][1,4]oxazine-7(4H)-carboxylate (60 mg, 0.15 mmol), 1-Methyl-1H-pyrazole-5-boronic acid pinacol ester (48 mg, 0.23 mmol), Na$_2$CO$_3$ (49 mg, 0.46 mmol) and Pd(Ph$_3$)$_4$ (16 mg, 0.015 mmol) and purged with Argon before a mixture of toluene:ethanol:water (3:3:1) (4.2 ml) was added. The resulting suspension was irradiated with microwaves at 100° C. for 18 min.

The reaction mixture was cooled down, diluted with DCM and concentrated under vacuum. The residue was purified by flash chromatography, silica gel, gradient hexane to hexane:acetone (6:4) to afford the desired product (19 mg, 36% yield).

$^1$H-NMR (400 MHz, CDCl$_3$), mixture of two rotamers, δ ppm: 7.52 (d, J=2 Hz, 1H) 6.15 (d, J=2 Hz, 1H), 5.28 (d, J=16 Hz, 1H), 5.09 (d, J=16 Hz, 1H), 4.5-4.2 (m, 2H), 4.23 (s, 3H), 4.0-3.9 (m, 2H), 3.56 (m, 1H), 3.40 (m, 1H), 1.50 (s, 9H).

This method was used for the preparation of intermediates of formula (V) in the synthesis of examples of formula (I) 64-66.

Example of Preparation of an Intermediate of Formula (VI)

Synthesis of (5aR,8aR)-3-(2-fluorophenyl)-4,5a,6,7,8,8a-hexahydropyrrolo[3,4-b][1,2,3]triazolo[1,5-d][1,4]oxazine

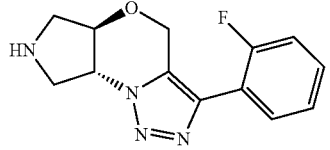 [SMILES: Fc1ccccc1-c1nnn2c1CO[C@@H]1CNC[C@H]12]

To a solution of (5aR,8aR)-tert-butyl-3-(2-fluorophenyl)-5a,6,8,8a-tetrahydropyrrolo[3,4-b][1,2,3]triazolo[1,5-d][1,4]oxazine-7(4H)-carboxylate (4.01 g, 11.1 mmol) in dioxane (28 ml), a solution of 4M HCl in dioxane (36.2 ml) was added and the mixture was stirred at r.t. for 3 h. The mixture was concentrated to dryness to afford the titled compound (3.52 g, 95% yield) as dihydrochloride.

$^1$H-NMR (400 MHz, MeOD) δ ppm: 7.85 (td, J=8, 1 Hz, 1H), 7.51 (m, 1H), 7.36 (td, J=8, 1 Hz, 1H), 7.28 (ddd, J=12, 8, 1 Hz, 1H), 5.44 (dd, J=16, 1 Hz, 1H), 5.28 (d, J=16 Hz, 1H), 4.71 (m, 1H), 4.5-4.3 (m, 2H), 3.87 (dd, J=11, 6 Hz, 1H), 3.76 (t, J=11 Hz, 1H), 3.46 (t, J=11 Hz, 1H).

Examples of Preparation of Compounds of General Formula (I), Method A

Example 14

(5aR,8aR)-3-(2-fluorophenyl)-7-((6-(trifluoromethyl)pyridin-3-yl)methyl)-4,5a,6,7,8,8a-hexahydropyrrolo[3,4-b][1,2,3]triazolo[1,5-d][1,4]oxazine hydrochloride

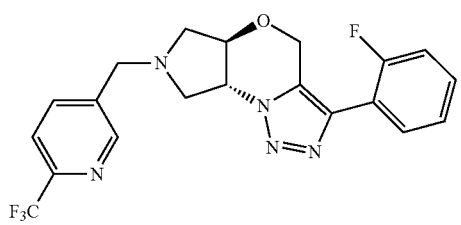 [SMILES: Fc1ccccc1-c1nnn2c1CO[C@@H]1CN(Cc3ccc(C(F)(F)F)nc3)C[C@H]12]

To a suspension of (5aR,8aR)-3-(2-fluorophenyl)-4,5a,6,7,8,8a-hexahydropyrrolo[3,4-b][1,2,3]triazolo[1,5-d][1,4]oxazine dihydrochloride (45 mg, 0.135 mmol) in DCE (2.2 ml), DIPEA (71 μl, 0.40 mmol) was added and the mixture was stirred at rt for 5 min. A solution of 6-(trifluoromethyl) nicotinaldehyde (35 mg, 0.2 mmol) in DCE (0.5 ml) and NaBH(OAc)$_3$ (57 mg, 0.27 mmol) were added and the reaction mixture was stirred at r.t. for 16 h. DCM was added and washed with NaHCO$_3$ sat. solution and brine, dried over Na$_2$SO$_4$, filtered and concentrated. Purification by flash chromatography, silica gel, gradient hexane to ethyl acetate afforded the desired product (53 mg, 94% yield).

The previous product (46 mg, 0.11 mmol) was dissolved in AcOEt (1 ml) and a 1.25 M solution of HCl in EtOH (88 μL, 0.11 mmol) was added. After 30 min of stirring, the mixture was concentrated to afford the hydrochloride as white solid (49 mg).

HPLC retention time: 6.15 min; HRMS: 420.1435 (M+H).

The examples 15, 16, 17, 18, 56, 57, 58, 59 were obtained diastereomerically and enantiomerically pure by semi-preparative HPLC (Chiralpak IA 250×10 mm, 5 μM, eluent: heptane/DCM/EtOH, 5 mL/min) of the corresponding mixtures of the diastereomers obtained by reaction of the enantiomerically pure intermediate (VI) and a racemic aldehyde (VII).

Example of Preparation of Compounds of General Formula (I), Method B a) ((5aS,8aS)-3-(2,4-difluorophenyl)-5a,6,8,8a-tetrahydropyrrolo[3,4-b][1,2,3]triazolo[1,5-d][1,4]oxazin-7(4H)-yl)(2,5-dimethylfuran-3-yl)methanone

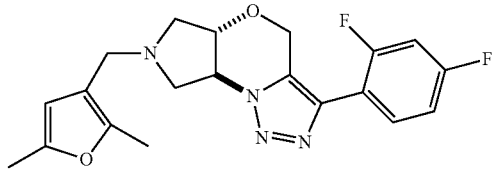

To a solution of (5aS,8aS)-3-(2,4-difluorophenyl)-4,5a,6,7,8,8a-hexahydropyrrolo[3,4-b][1,2,3]triazolo[1,5-d][1,4]oxazine dihydrochloride (80 mg, 0.25 mmol) and DIPEA (115 μl 0.66 mmol) in DCM (12 ml), 2,5-dimethylfuran-3-carbonyl chloride (43 μL, 0.33 mmol) was slowly added at 0° C., and the mixture was stirred at rt under nitrogen overnight. DCM was added and washed with saturated solution of NaHCO$_3$ and brine, dried over MgSO$_4$, filtered and concentrated to dryness. Purification by flash chromatography, silica gel, gradient hexane to ethyl acetate afforded the desired product (100 mg, 99% yield). $^1$H-NMR (400 MHz, CDCl$_3$) δ ppm: 7.97 (m, 1H) 7.03 (td, J=8, 2 Hz, 1H), 6.91 (t, J=9 Hz, 1H), 6.05 (s, 1H), 5.32 (d, J=16 Hz, 1H), 5.16 (m, 1H), 4.63 (m, 1H), 4.40 (m, 1H), 4.12 (m, 2H), 3.84 (m, 1H), 3.66 (m,1H), 2.47 (s, 3H), 2.28 (s, 3H).

b) Example 22

(5aS,8aS)-3-(2,4-difluorophenyl)-7-((2,5-dimethylfuran-3-yl)methyl)-4,5a,6,7,8,8a-hexahydropyrrolo[3,4-b][1,2,3]triazolo[1,5-d][1,4]oxazine hydrochloride

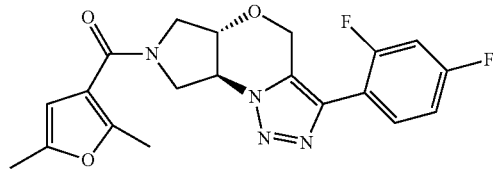 [SMILES: Cc1cc(C(=O)N2C[C@@H]3OCc4c(-c5ccc(F)cc5F)nnn4[C@H]3C2)c(C)o1]

To a 1 M solution of borane in THF (1.1 mL; 1.09 mmol) cooled at 0° C. under nitrogen atmosphere, a solution of ((5aS,8aS)-3-(2,4-difluorophenyl)-5a,6,8,8a-tetrahydropyrrolo[3,4-b][1,2,3]triazolo[1,5-d][1,4]oxazin-7(4H)-yl)(2,5-dimethylfuran-3-yl)methanone (87 mg, 0.22 mmol) in dry THF (2.6 ml) was added. The resulting mixture was stirred at reflux overnight. Methanol (2 ml) and 10% KOH solution (1 ml) was added at 0° C. and refluxed for one hour. The reaction mixture was concentrated under vacuum and the residue was diluted with DCM and washed with brine. The organic layer was dried over Na$_2$SO$_4$, filtered and the solvent was removed under reduced pressure. Purification by flash chromatography, silica gel, gradient hexane to ethyl acetate afforded the desired product (27 mg, 32% yield). The previous product (27 mg, 0.07 mmol) was dissolved in AcOEt (1 ml) and a 1.25 M solution of HCl in EtOH (56 μL, 0.07 mmol) was added. After 30 min of stirring, the mixture was concentrated to afford the hydrochloride as a white solid (28 mg). HPLC retention time: 5.85 min; HRMS: 387.1647 (M+H)

This method was used for the preparation of examples of formula (I) 22-23.

Table I below, discloses compounds prepared according to the aforementioned methods:

TABLE I

| Example | Structure | Name | Kin. Solub. (μM) | HPLC (retention time, min) | HRMS |
|---|---|---|---|---|---|
| 1 | 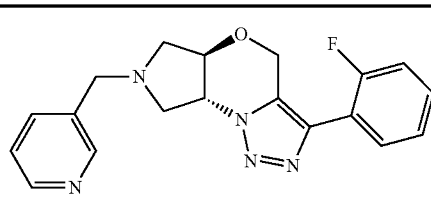 | (5aR,8aR)-3-(2-fluorophenyl)-7-(pyridin-3-ylmethyl)-4,5a,6,7,8,8a-hexahydropyrrolo[3,4-b][1,2,3]triazolo[1,5-d][1,4]oxazine hydrochloride ·HCl | >20.00 | 4.81 | 352.1577 (M + H) |

TABLE I-continued

| Example | Structure | Name | Kin. Solub. (μM) | HPLC (retention time, min) | HRMS |
|---|---|---|---|---|---|
| 2 | 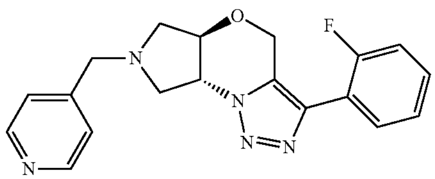 | (5aRS,8aRS)-3-(2-fluorophenyl)-7-(pyridin-4-ylmethyl)-4,5a,6,7,8,8a-hexahydropyrrolo[3,4-b][1,2,3]triazolo[1,5-d][1,4]oxazine hydrochloride | >10.00 | 4.82 | 352.1584 (M + H) |
| 3 | 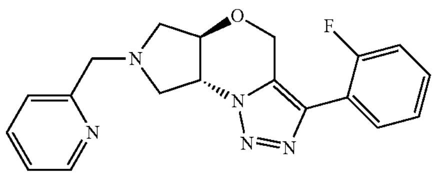 | (5aRS,8aRS)-3-(2-fluorophenyl)-7-(pyridin-2-ylmethyl)-4,5a,6,7,8,8a-hexahydropyrrolo[3,4-b][1,2,3]triazolo[1,5-d][1,4]oxazine hydrochloride | >10.00 | 5.09 | 352.1583 (M + H) |
| 4 | 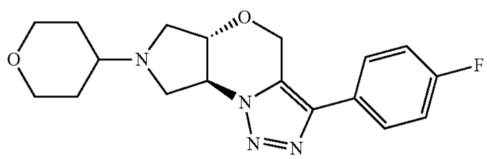 | (5aS,8aS)-3-(4-fluorophenyl)-7-(tetrahydro-2H-pyran-4-yl)-4,5a,6,7,8,8a-hexahydropyrrolo[3,4-b][1,2,3]triazolo[1,5-d][1,4]oxazine hydrochloride | >10.00 | 4.93 | 345.1733 (M + H) |
| 5 | 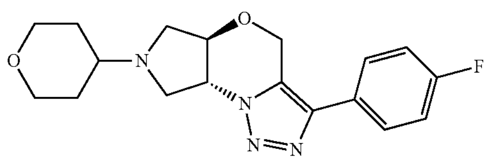 | (5aR,8aR)-3-(4-fluorophenyl)-7-(tetrahydro-2H-pyran-4-yl)-4,5a,6,7,8,8a-hexahydropyrrolo[3,4-b][1,2,3]triazolo[1,5-d][1,4]oxazine hydrochloride | >10.00 | 4.92 | 345.1733 (M + H) |
| 6 | 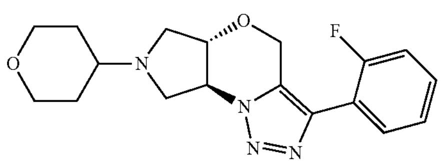 | (5aS,8aS)-3-(2-fluorophenyl)-7-(tetrahydro-2H-pyran-4-yl)-4,5a,6,7,8,8a-hexahydropyrrolo[3,4-b][1,2,3]triazolo[1,5-d][1,4]oxazine hydrochloride | >10.00 | 4.80 | 367.1558 (M + Na) |
| 7 | 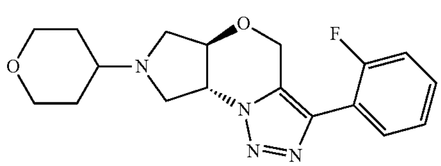 | (5aR,8aR)-3-(2-fluorophenyl)-7-(tetrahydro-2H-pyran-4-yl)-4,5a,6,7,8,8a-hexahydropyrrolo[3,4-b][1,2,3]triazolo[1,5-d][1,4]oxazine hydrochloride | >10.00 | 4.79 | 367.1558 (M + Na) |
| 8 | 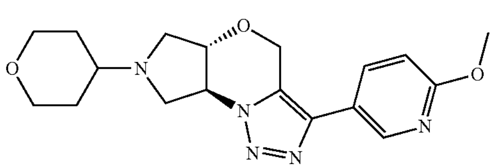 | (5aS,8aS)-3-(6-methoxypyridin-3-yl)-7-(tetrahydro-2H-pyran-4-yl)-4,5a,6,7,8,8a-hexahydropyrrolo[3,4-b][1,2,3]triazolo[1,5-d][1,4]oxazine hydrochloride | >10.00 | 4.41 | 380.1680 (M + Na) |

TABLE I-continued

| Example | Structure | Name | Kin. Solub. (μM) | HPLC (retention time, min) | HRMS |
|---|---|---|---|---|---|
| 9 | 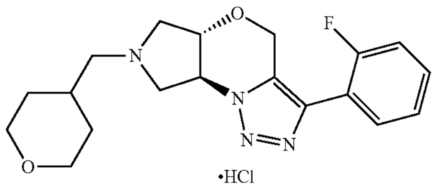 [SMILES: Fc1ccccc1-c1nnn2c1CO[C@H]1CN(CC3CCOCC3)C[C@@H]12 ; Cl] | (5aS,8aS)-3-(2-fluorophenyl)-7-((tetrahydro-2H-pyran-4-yl)methyl)-4,5a,6,7,8,8a-hexahydropyrrolo[3,4-b][1,2,3]triazolo[1,5-d][1,4]oxazine hydrochloride | >10.00 | 4.80 | 359.1865 (M + H) |
| 10 | 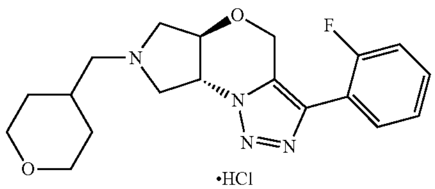 [SMILES: Fc1ccccc1-c1nnn2c1CO[C@@H]1CN(CC3CCOCC3)C[C@H]12 ; Cl] | (5aR,8aR)-3-(2-fluorophenyl)-7-((tetrahydro-2H-pyran-4-yl)methyl)-4,5a,6,7,8,8a-hexahydropyrrolo[3,4-b][1,2,3]triazolo[1,5-d][1,4]oxazine hydrochloride | >10.00 | 4.86 | 359.1886 (M + H) |
| 11 | 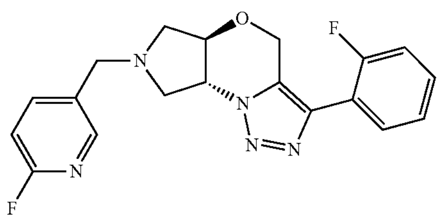 | (5aR,8aR)-3-(2-fluorophenyl)-7-((6-fluoropyridin-3-yl)methyl)-4,5a,6,7,8,8a-hexahydropyrrolo[3,4-b][1,2,3]triazolo[1,5-d][1,4]oxazine hydrochloride | >10.00 | 5.23 | 370.1490 (M + H) |
| 12 | 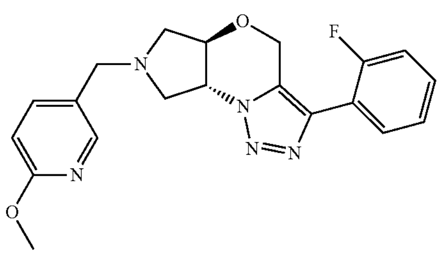 [SMILES: Fc1ccc(CN2C[C@@H]3[C@@H](C2)OCc2c(-c4ccccc4F)nnn23)cn1 ; Cl] | (5aR,8aR)-3-(2-fluorophenyl)-7-((6-methoxypyridin-3-yl)methyl)-4,5a,6,7,8,8a-hexahydropyrrolo[3,4-b][1,2,3]triazolo[1,5-d][1,4]oxazine hydrochloride | >10.00 | 5.26 | 382.1962 (M + H) |
| 13 | 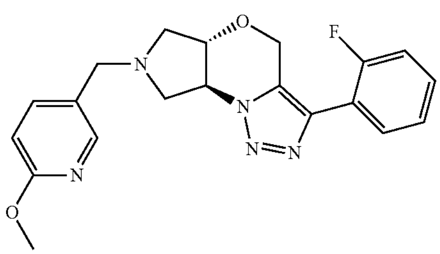 [SMILES: Fc1ccc(CN2C[C@@H]3OCc4c(-c5ccccn5)nnn4[C@H]3C2)cc1 ; Cl] | (5aS,8aS)-3-(2-fluorophenyl)-7-((6-methoxypyridin-3-yl)methyl)-4,5a,6,7,8,8a-hexahydropyrrolo[3,4-b][1,2,3]triazolo[1,5-d][1,4]oxazine hydrochloride | >10.00 | 5.29 | 382.1693 (M + H) |
| 14 | 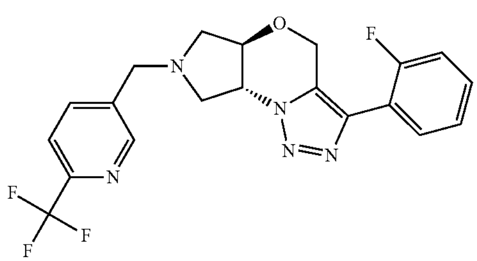 | (5aR,8aR)-3-(2-fluorophenyl)-7-((6-(trifluoromethyl)pyridin-3-yl)methyl)-4,5a,6,7,8,8a-hexahydropyrrolo[3,4-b][1,2,3]triazolo[1,5-d][1,4]oxazine hydrochloride | >10.00 | 6.15 | 420.1435 (M + H) |

TABLE I-continued

| Example | Structure | Name | Kin. Solub. (μM) | HPLC (retention time, min) | HRMS |
|---|---|---|---|---|---|
| 15 | •HCl | (5aS,8aS)-3-(2-fluorophenyl)-7-(((R)-tetrahydrofuran-3-yl)methyl)-4,5a,6,7,8,8a-hexahydropyrrolo[3,4-b][1,2,3]triazolo[1,5-d][1,4]oxazine hydrochloride | >10.00 | 4.83 | 345.1733 (M + H) |
| 16 | •HCl | (5aR,8aR)-3-(2-fluorophenyl)-7-(((S)-tetrahydrofuran-3-yl)methyl)-4,5a,6,7,8,8a-hexahydropyrrolo[3,4-b][1,2,3]triazolo[1,5-d][1,4]oxazine hydrochloride | >10.00 | 4.83 | 345.1737 (M + H) |
| 17 | •HCl | (5aS,8aS)-3-(2-fluorophenyl)-7-(((S)-tetrahydrofuran-3-yl)methyl)-4,5a,6,7,8,8a-hexahydropyrrolo[3,4-b][1,2,3]triazolo[1,5-d][1,4]oxazine hydrochloride | >10.00 | 4.81 | 345.1734 (M + H) |
| 18 | •HCl | (5aR,8aR)-3-(2-fluorophenyl)-7-(((R)-tetrahydrofuran-3-yl)methyl)-4,5a,6,7,8,8a-hexahydropyrrolo[3,4-b][1,2,3]triazolo[1,5-d][1,4]oxazine hydrochloride | >10.00 | 4.83 | 345.1744 (M + H) |
| 19 | •HCl | (5aR,8aR)-7-((6-ethoxypyridin-3-yl)methyl)-3-(2-fluorophenyl)-4,5a,6,7,8,8a-hexahydropyrrolo[3,4-b][1,2,3]triazolo[1,5-d][1,4]oxazine hydrochloride | >10.00 | 5.56 | 396.1852 (M + H) |
| 20 | •HCl | (5aS,8aS)-7-((6-ethoxypyridin-3-yl)methyl)-3-(2-fluorophenyl)-4,5a,6,7,8,8a-hexahydropyrrolo[3,4-b][1,2,3]triazolo[1,5-d][1,4]oxazine hydrochloride | >10.00 | 5.55 | 396.1840 (M + H) |

TABLE I-continued

| Example | Structure | Name | Kin. Solub. (μM) | HPLC (retention time, min) | HRMS |
|---|---|---|---|---|---|
| 21 | 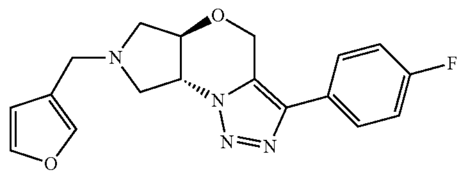 | (5aRS,8aRS)-3-(4-fluorophenyl)-7-(furan-3-ylmethyl)-4,5a,6,7,8,8a-hexahydropyrrolo[3,4-b][1,2,3]triazolo[1,5-d][1,4]oxazine hydrochloride | >10.00 | 5.29 | 341.1426 (M + H) |
| 22 | 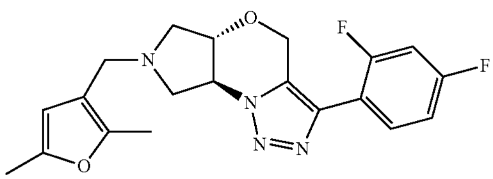 | (5aS,8aS)-3-(2,4-difluorophenyl)-7-((2,5-dimethylfuran-3-yl)methyl)-4,5a,6,7,8,8a-hexahydropyrrolo[3,4-b][1,2,3]triazolo[1,5-d][1,4]oxazine hydrochloride | >10.00 | 5.85 | 387.1647 (M + H) |
| 23 | 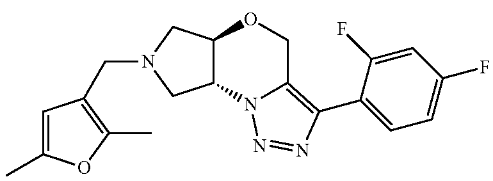 | (5aR,8aR)-3-(2,4-difluorophenyl)-7-((2,5-dimethylfuran-3-yl)methyl)-4,5a,6,7,8,8a-hexahydropyrrolo[3,4-b][1,2,3]triazolo[1,5-d][1,4]oxazine hydrochloride | >10.00 | 5.85 | 387.1648 (M + H) |
| 24 | 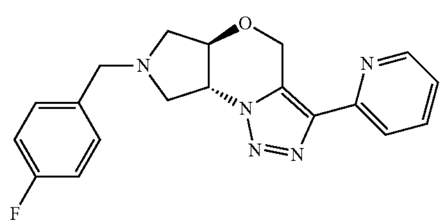 | (5aR,8aR)-7-(4-fluorobenzyl)-3-(pyridin-2-yl)-4,5a,6,7,8,8a-hexahydropyrrolo[3,4-b][1,2,3]triazolo[1,5-d][1,4]oxazine hydrochloride | >10.00 | 5.16 | 352.1570 (M + H) |
| 25 | 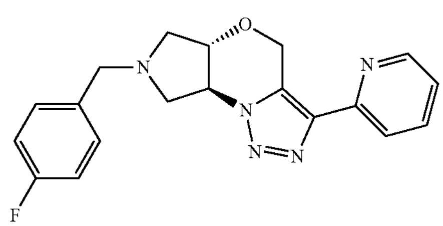 | (5aS,8aS)-7-(4-fluorobenzyl)-3-(pyridin-2-yl)-4,5a,6,7,8,8a-hexahydropyrrolo[3,4-b][1,2,3]triazolo[1,5-d][1,4]oxazine hydrochloride | >10.00 | 5.13 | 374.1396 (M + Na) |
| 26 | 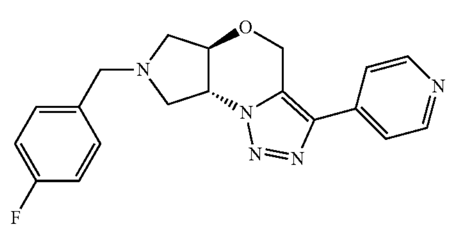 | (5aRS,8aRS)-7-(4-fluorobenzyl)-3-(pyridin-4-yl)-4,5a,6,7,8,8a-hexahydropyrrolo[3,4-b][1,2,3]triazolo[1,5-d][1,4]oxazine hydrochloride | >10.00 | 4.11 | 352.1574 (M + H) |

TABLE I-continued

| Example | Structure | Name | Kin. Solub. (μM) | HPLC (retention time, min) | HRMS |
|---|---|---|---|---|---|
| 27 | ·HCl | (5aS,8aS)-3-(2,4-difluorophenyl)-7-(tetrahydro-2H-pyran-4-yl)-4,5a,6,7,8,8a-hexahydropyrrolo[3,4-b][1,2,3]triazolo[1,5-d][1,4]oxazine hydrochloride | >10.00 | 4.96 | 363.1639 (M + H) |
| 28 | ·HCl | (5aR,8aR)-3-(2,4-difluorophenyl)-7-(tetrahydro-2H-pyran-4-yl)-4,5a,6,7,8,8a-hexahydropyrrolo[3,4-b][1,2,3]triazolo[1,5-d][1,4]oxazine hydrochloride | >10.00 | 4.93 | 363.1639 (M + H) |
| 29 | ·HCl | (5aR,8aR)-7-(4-fluorobenzyl)-3-(3-fluoropyridin-2-yl)-4,5a,6,7,8,8a-hexahydropyrrolo[3,4-b][1,2,3]triazolo[1,5-d][1,4]oxazine hydrochloride | >10.00 | 5.17 | 370.1466 (M + H) |
| 30 | ·HCl | (5aS,8aS)-3-(5-fluoropyridin-2-yl)-7-(tetrahydro-2H-pyran-4-yl)-4,5a,6,7,8,8a-hexahydropyrrolo[3,4-b][1,2,3]triazolo[1,5-d][1,4]oxazine hydrochloride | >10.00 | 4.73 | 346.1663 (M + H) |
| 31 | ·HCl | (5aS,8aS)-3-(pyridin-2-yl)-7-(tetrahydro-2H-pyran-4-yl)-4,5a,6,7,8,8a-hexahydropyrrolo[3,4-b][1,2,3]triazolo[1,5-d][1,4]oxazine hydrochloride | >10.00 | 4.22 | 328.1763 (M + H) |
| 32 | ·HCl | (5aR,8aR)-7-benzyl-3-(pyridin-2-yl)-4,5a,6,7,8,8a-hexahydropyrrolo[3,4-b][1,2,3]triazolo[1,5-d][1,4]oxazine hydrochloride | >10.00 | 4.99 | 334.1663 (M + H) |
| 33 | ·HCl | (5aS,8aS)-7-benzyl-3-(pyridin-2-yl)-4,5a,6,7,8,8a-hexahydropyrrolo[3,4-b][1,2,3]triazolo[1,5-d][1,4]oxazine hydrochloride | >10.00 | 5.04 | 334.1654 (M + H) |

TABLE I-continued

| Example | Structure | Name | Kin. Solub. (μM) | HPLC (retention time, min) | HRMS |
|---|---|---|---|---|---|
| 34 | 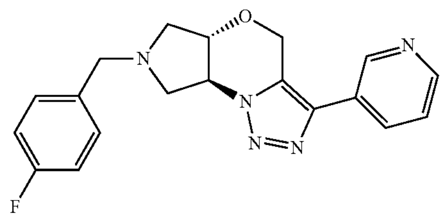 | (5aS,8aS)-7-(4-fluorobenzyl)-3-(pyridin-3-yl)-4,5a,6,7,8,8a-hexahydropyrrolo[3,4-b][1,2,3]triazolo[1,5-d][1,4]oxazine hydrochloride | >10.00 | 4.16 | 352.1586 (M + H) |
| 35 | 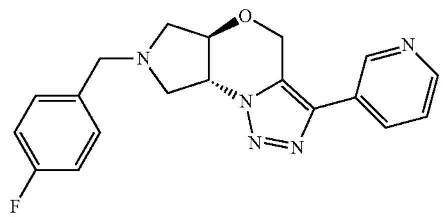 | (5aR,8aR)-7-(4-fluorobenzyl)-3-(pyridin-3-yl)-4,5a,6,7,8,8a-hexahydropyrrolo[3,4-b][1,2,3]triazolo[1,5-d][1,4]oxazine hydrochloride | >10.00 | 4.16 | 352.1575 (M + H) |
| 36 | 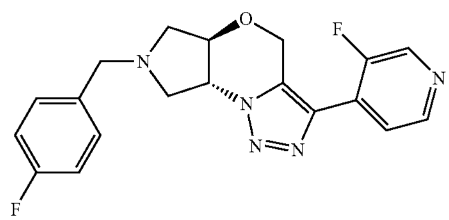 | (5aR,8aR)-7-(4-fluorobenzyl)-3-(3-fluoropyridin-4-yl)-4,5a,6,7,8,8a-hexahydropyrrolo[3,4-b][1,2,3]triazolo[1,5-d][1,4]oxazine hydrochloride | >10.00 | 4.80 | 370.1491 (M + H) |
| 37 | 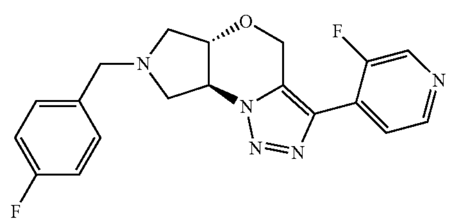 | (5aS,8aS)-7-(4-fluorobenzyl)-3-(3-fluoropyridin-4-yl)-4,5a,6,7,8,8a-hexahydropyrrolo[3,4-b][1,2,3]triazolo[1,5-d][1,4]oxazine hydrochloride | >10.00 | 4.80 | 370.1474 (M + H) |
| 38 | 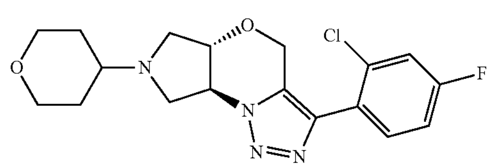 | (5aS,8aS)-3-(2-chloro-4-fluorophenyl)-7-(tetrahydro-2H-pyran-4-yl)-4,5a,6,7,8,8a-hexahydropyrrolo[3,4-b][1,2,3]triazolo[1,5-d][1,4]oxazine hydrochloride | >10.00 | 5.02 | 379.1320 (M + H) |
| 39 | 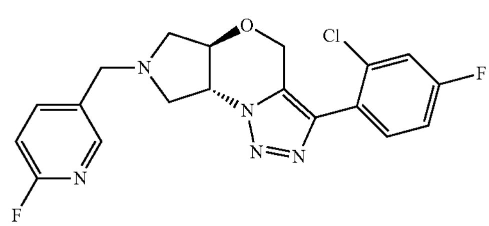 | (5aR,8aR)-3-(2-chloro-4-fluorophenyl)-7-((6-fluoropyridin-3-yl)methyl)-4,5a,6,7,8,8a-hexahydropyrrolo[3,4-b][1,2,3]triazolo[1,5-d][1,4]oxazine hydrochloride | >10.00 | 5.49 | 404.1096 (M + H) |

TABLE I-continued

| Example | Structure | Name | Kin. Solub. (μM) | HPLC (retention time, min) | HRMS |
|---|---|---|---|---|---|
| 40 | 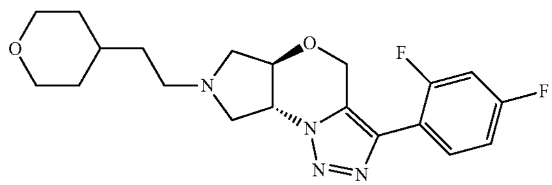 | (5aR,8aR)-3-(2,4-difluorophenyl)-7-(2-(tetrahydro-2H-pyran-4-yl)ethyl)-4,5a,6,7,8,8a-hexahydropyrrolo[3,4-b][1,2,3]triazolo[1,5-d][1,4]oxazine hydrochloride | >10.00 | 5.20 | 391.1942 (M + H) |
| 41 | 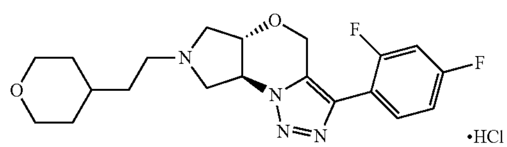 [SMILES: Fc1ccc(-c2nnn3c2CO[C@H]2CN(CCC4CCOCC4)C[C@@H]23)c(F)c1 ; Cl] | (5aS,8aS)-3-(2,4-difluorophenyl)-7-(2-(tetrahydro-2H-pyran-4-yl)ethyl)-4,5a,6,7,8,8a-hexahydropyrrolo[3,4-b][1,2,3]triazolo[1,5-d][1,4]oxazine hydrochloride | >10.00 | 5.20 | 391.1953 (M + H) |
| 42 | 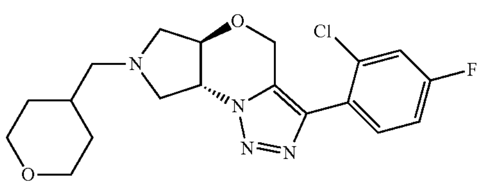 | (5aR,8aR)-3-(2-chloro-4-fluorophenyl)-7-((tetrahydro-2H-pyran-4-yl)methyl)-4,5a,6,7,8,8a-hexahydropyrrolo[3,4-b][1,2,3]triazolo[1,5-d][1,4]oxazine hydrochloride | >10.00 | 5.15 | 393.1502 (M + H) |
| 43 | 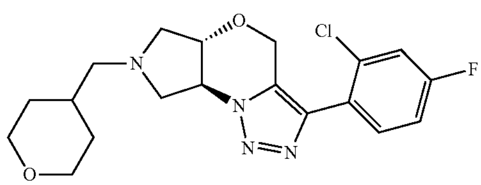 | (5aS,8aS)-3-(2-chloro-4-fluorophenyl)-7-((tetrahydro-2H-pyran-4-yl)methyl)-4,5a,6,7,8,8a-hexahydropyrrolo[3,4-b][1,2,3]triazolo[1,5-d][1,4]oxazine hydrochloride | >10.00 | 5.19 | 393.1502 (M + H) |
| 44 | 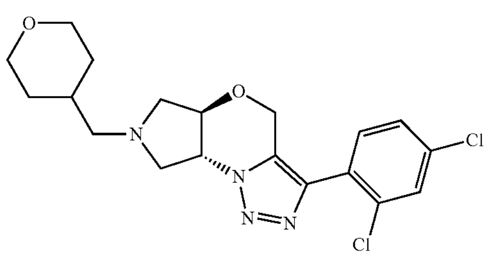 | (5aR,8aR)-3-(2,4-dichlorophenyl)-7-((tetrahydro-2H-pyran-4-yl)methyl)-4,5a,6,7,8,8a-hexahydropyrrolo[3,4-b][1,2,3]triazolo[1,5-d][1,4]oxazine hydrochloride | >10.00 | 5.52 | 409.1196 (M + H) |
| 45 | 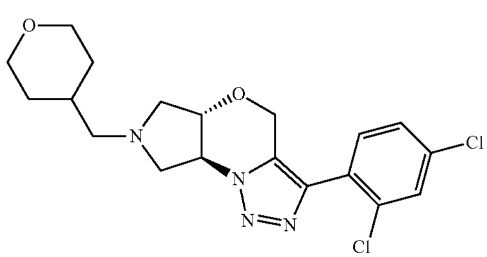 | (5aS,8aS)-3-(2,4-dichlorophenyl)-7-((tetrahydro-2H-pyran-4-yl)methyl)-4,5a,6,7,8,8a-hexahydropyrrolo[3,4-b][1,2,3]triazolo[1,5-d][1,4]oxazine hydrochloride | >10.00 | 5.52 | 409.1181 (M + H) |

TABLE I-continued

| Example | Structure | Name | Kin. Solub. (μM) | HPLC (retention time, min) | HRMS |
|---|---|---|---|---|---|
| 46 | (structure) ·HCl | (5aS,8aS)-3-(2,4-dichlorophenyl)-7-(tetrahydro-2H-pyran-4-yl)-4,5a,6,7,8,8a-hexahydropyrrolo[3,4-b][1,2,3]triazolo[1,5-d][1,4]oxazine hydrochloride | >10.00 | 5.42 | 395.1043 (M + H) |
| 47 | (structure) ·HCl | (5aR,8aR)-3-(2-chloro-4-fluorophenyl)-7-(2-(tetrahydro-2H-pyran-4-yl)ethyl)-4,5a,6,7,8,8a-hexahydropyrrolo[3,4-b][1,2,3]triazolo[1,5-d][1,4]oxazine hydrochloride | >10.00 | 5.32 | 407.1669 (M + H) |
| 48 | (structure) ·HCl | (5aS,8aS)-3-(2-chloro-4-fluorophenyl)-7-(2-(tetrahydro-2H-pyran-4-yl)ethyl)-4,5a,6,7,8,8a-hexahydropyrrolo[3,4-b][1,2,3]triazolo[1,5-d][1,4]oxazine hydrochloride | >10.00 | 5.33 | 407.1647 (M + H) |
| 49 | (structure) ·HCl | (5aR,8aR)-3-(2-chloro-4-fluorophenyl)-7-((6-methoxypyridin-3-yl)methyl)-4,5a,6,7,8,8a-hexahydropyrrolo[3,4-b][1,2,3]triazolo[1,5-d][1,4]oxazine hydrochloride | >10.00 | 5.51 | 416.1284 (M + H) |
| 50 | (structure) ·HCl | (5aS,8aS)-3-(2-chloro-4-fluorophenyl)-7-((6-methoxypyridin-3-yl)methyl)-4,5a,6,7,8,8a-hexahydropyrrolo[3,4-b][1,2,3]triazolo[1,5-d][1,4]oxazine hydrochloride | >10.00 | 5.50 | 416.1285 (M + H) |
| 51 | (structure) ·HCl | (5aR,8aR)-3-(2,4-difluorophenyl)-7-((6-methoxypyridin-3-yl)methyl)-4,5a,6,7,8,8a-hexahydropyrrolo[3,4-b][1,2,3]triazolo[1,5-d][1,4]oxazine hydrochloride | >10.00 | 5.41 | 400.1596 (M + H) |

TABLE I-continued

| Example | Structure | Name | Kin. Solub. (μM) | HPLC (retention time, min) | HRMS |
|---|---|---|---|---|---|
| 52 | 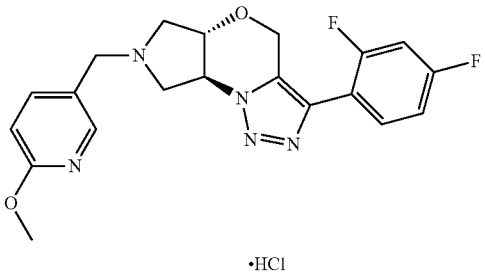 [SMILES: COc1ccc(CN2C[C@@H]3OCc4c(-c5ccc(F)cc5F)nnn4[C@H]3C2)cn1 ; Cl] | (5aS,8aS)-3-(2,4-difluorophenyl)-7-((6-methoxypyridin-3-yl)methyl)-4,5a,6,7,8,8a-hexahydropyrrolo[3,4-b][1,2,3]triazolo[1,5-d][1,4]oxazine hydrochloride | >10.00 | 5.42 | 400.1585 (M + H) |
| 53 | 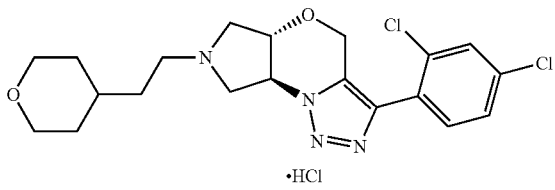 [SMILES: Clc1ccc(-c2nnn3c2CO[C@H]2CN(CCC4CCOCC4)C[C@@H]23)c(Cl)c1 ; Cl] | (5aS,8aS)-3-(2,4-dichlorophenyl)-7-(2-(tetrahydro-2H-pyran-4-yl)ethyl)-4,5a,6,7,8,8a-hexahydropyrrolo[3,4-b][1,2,3]triazolo[1,5-d][1,4]oxazine hydrochloride | >10.00 | 5.65 | 423.1351 (M + H) |
| 54 | 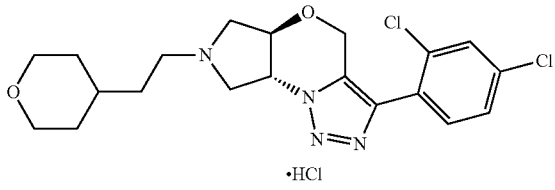 [SMILES: Clc1ccc(-c2nnn3c2CO[C@@H]2CN(CCC4CCOCC4)C[C@H]23)c(Cl)c1 ; Cl] | (5aR,8aR)-3-(2,4-dichlorophenyl)-7-(2-(tetrahydro-2H-pyran-4-yl)ethyl)-4,5a,6,7,8,8a-hexahydropyrrolo[3,4-b][1,2,3]triazolo[1,5-d][1,4]oxazine hydrochloride | >10.00 | 5.65 | 423.1341 (M + H) |
| 55 | 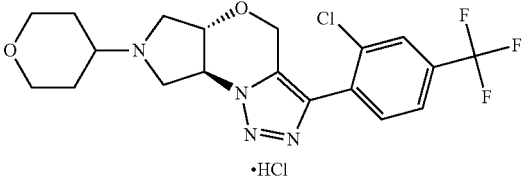 [SMILES: FC(F)(F)c1ccc(-c2nnn3c2CO[C@H]2CN(C4CCOCC4)C[C@@H]23)c(Cl)c1 ; Cl] | (5aS,8aS)-3-(2-chloro-4-(trifluoromethyl)phenyl)-7-(tetrahydro-2H-pyran-4-yl)-4,5a,6,7,8,8a-hexahydropyrrolo[3,4-b][1,2,3]triazolo[1,5-d][1,4]oxazine hydrochloride | >10.00 | 5.68 | 429.1316 (M + H) |
| 56 | 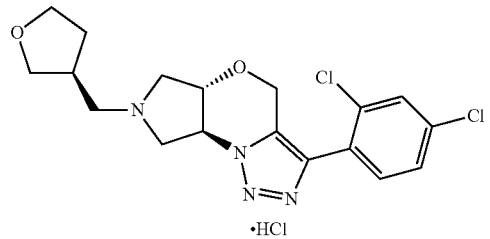 [SMILES: Clc1ccc(-c2nnn3c2CO[C@H]2CN(C[C@@H]4CCOC4)C[C@@H]23)c(Cl)c1 ; Cl] | (5aS,8aS)-3-(2,4-dichlorophenyl)-7-(((S)-tetrahydrofuran-3-yl)methyl)-4,5a,6,7,8,8a-hexahydropyrrolo[3,4-b][1,2,3]triazolo[1,5-d][1,4]oxazine hydrochloride | >10.00 | 5.46 | 395.1038 (M + H) |
| 57 | 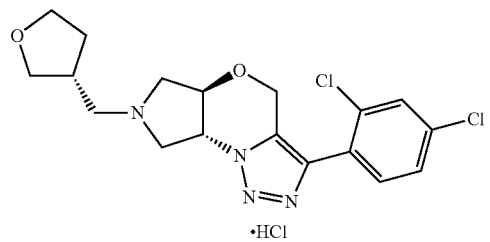 [SMILES: Clc1ccc(-c2nnn3c2CO[C@@H]2CN(C[C@H]4CCOC4)C[C@H]23)c(Cl)c1 ; Cl] | (5aR,8aR)-3-(2,4-dichlorophenyl)-7-(((R)-tetrahydrofuran-3-yl)methyl)-4,5a,6,7,8,8a-hexahydropyrrolo[3,4-b][1,2,3]triazolo[1,5-d][1,4]oxazine hydrochloride | >10.00 | 5.46 | 395.1030 (M + H) |

TABLE I-continued

| Example | Structure | Name | Kin. Solub. (μM) | HPLC (retention time, min) | HRMS |
|---|---|---|---|---|---|
| 58 | 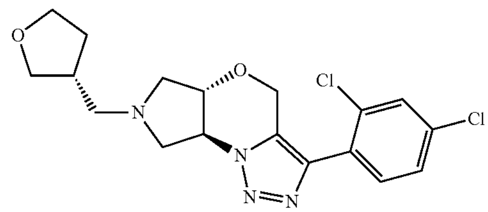 | (5aS,8aS)-3-(2,4-dichlorophenyl)-7-(((R)-tetrahydrofuran-3-yl)methyl)-4,5a,6,7,8,8a-hexahydropyrrolo[3,4-b][1,2,3]triazolo[1,5-d][1,4]oxazine hydrochloride | >10.00 | 5.44 | 395.1027 (M + H) |
| 59 | 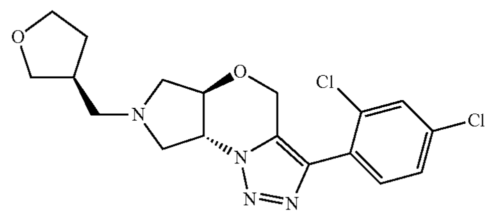 | (5aR,8aR)-3-(2,4-dichlorophenyl)-7-(((S)-tetrahydrofuran-3-yl)methyl)-4,5a,6,7,8,8a-hexahydropyrrolo[3,4-b][1,2,3]triazolo[1,5-d][1,4]oxazine hydrochloride | >10.00 | 5.46 | 395.1027 (M + H) |
| 60 | 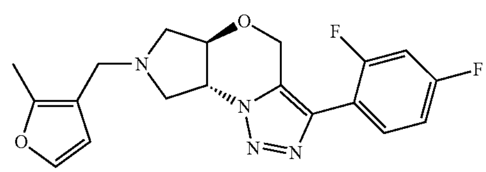 | (5aR,8aR)-3-(2,4-difluorophenyl)-7-((2-methylfuran-3-yl)methyl)-4,5a,6,7,8,8a-hexahydropyrrolo[3,4-b][1,2,3]triazolo[1,5-d][1,4]oxazine hydrochloride | >10.00 | 5.63 | 373.1481 (M + H) |
| 61 | 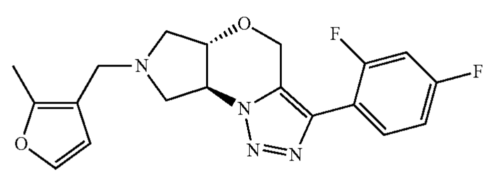 | (5aS,8aS)-3-(2,4-difluorophenyl)-7-((2-methylfuran-3-yl)methyl)-4,5a,6,7,8,8a-hexahydropyrrolo[3,4-b][1,2,3]triazolo[1,5-d][1,4]oxazine hydrochloride | >10.00 | 5.67 | 373.1473 (M + H) |
| 62 | 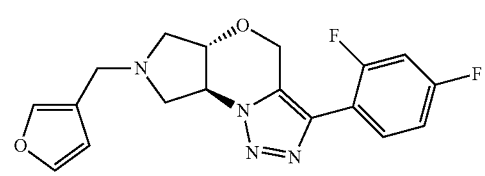 | (5aS,8aS)-3-(2,4-difluorophenyl)-7-(furan-3-ylmethyl)-4,5a,6,7,8,8a-hexahydropyrrolo[3,4-b][1,2,3]triazolo[1,5-d][1,4]oxazine hydrochloride | >10.00 | 5.39 | 359.1302 (M + H) |
| 63 | 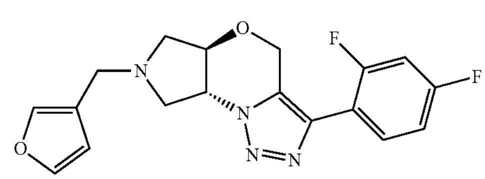 | (5aR,8aR)-3-(2,4-difluorophenyl)-7-(furan-3-ylmethyl)-4,5a,6,7,8,8a-hexahydropyrrolo[3,4-b][1,2,3]triazolo[1,5-d][1,4]oxazine hydrochloride | >10.00 | 5.34 | 359.1330 (M + H) |

TABLE I-continued

| Example | Structure | Name | Kin. Solub. (μM) | HPLC (retention time, min) | HRMS |
|---|---|---|---|---|---|
| 64 | (structure) ·HCl | (5aR,8aR)-7-(4-fluorobenzyl)-3-(tetrahydro-2H-pyran-4-yl)-4,5a,6,7,8,8a-hexahydropyrrolo[3,4-b][1,2,3]triazolo[1,5-d][1,4]oxazine hydrochloride | >10.00 | 4.65 | 359.1888 (M + H) |
| 65 | (structure) ·HCl | (5aS,8aS)-7-(4-fluorobenzyl)-3-(tetrahydro-2H-pyran-4-yl)-4,5a,6,7,8,8a-hexahydropyrrolo[3,4-b][1,2,3]triazolo[1,5-d][1,4]oxazine hydrochloride | >10.00 | 4.67 | 359.1894 (M + H) |
| 66 | (structure) ·HCl | (5aR,8aR)-7-(4-fluorobenzyl)-3-(1-methyl-1H-pyrazol-5-yl)-4,5a,6,7,8,8a-hexahydropyrrolo[3,4-b][1,2,3]triazolo[1,5-d][1,4]oxazine hydrochloride | >10.00 | 4.85 | 355.1686 (M + H) |

Analytical HPLC were performed using ZORBAX Eclipse XDB-C18 (4.6×150 mm, 5 μm) columns; flux: 1 ml/min.; A: H$_2$O (0.05% TFA). B: ACN; conditions: 1st Gradient 5% to 95% B in 7 min., 2nd Isocratic 95% B 5 min.

Solubility Study

Kinetic Solubility

To a buffered aqueous solution at pH=7.4 (1 mL), a 10 mM DMSO solution of the test compound (10 μL) was added and the mixture stirred for 4 hours. After centrifugation, the compound concentration in the supernatant was determined by liquid chromatography by fitting in a calibration curve of the compound.

Results regarding the solubility of the different compounds are shown in table I above.

In addition, the following table II provides some comparative examples where compounds of the present invention are compared in their kinetic solubility to compounds of general formula (I) prior art document WO2009/071657.

| Compound of the present invention | Kin. Solub. (μM) | Compound of WO2009071657 | Kin. Solub. (μM) |
|---|---|---|---|
| Example 1 (structure) ·HCl | >20.00 | (structure) | 4.18 |

-continued
| Compound of the present invention | Kin. Solub. (μM) | Compound of WO2009071657 | Kin. Solub. (μM) |
|---|---|---|---|
| Example 10 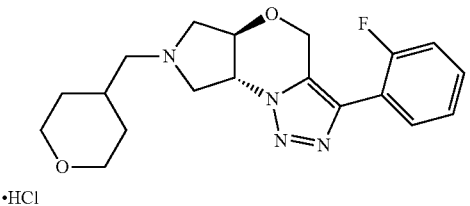 [SMILES: Fc1ccccc1-c1nnn2c1CO[C@@H]1CN(CC3CCOCC3)C[C@H]12 ; Cl] ·HCl | >10.00 | | |
| Example 16 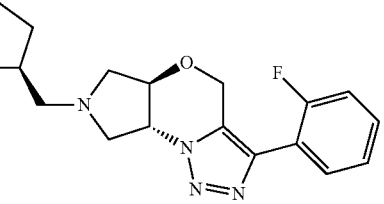 ·HCl | >10.00 | | |
| Example 5 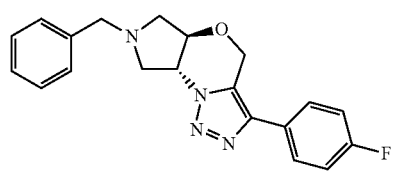 [SMILES: Fc1ccc(-c2nnn3c2CO[C@@H]2CN(Cc4ccccc4)C[C@H]23)cc1] ·HCl | >10.00 | 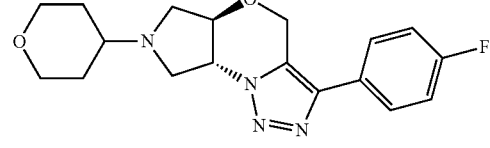 | 1.82 |
| Example 21 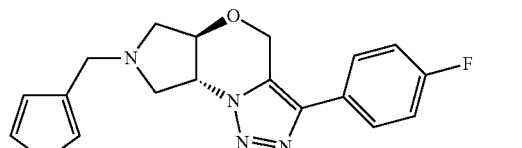 ·HCl | >10.00 | | |
| Example 23 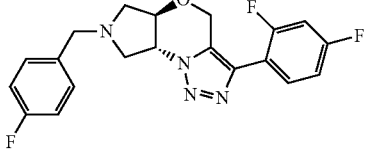 ·HCl | >10.00 | 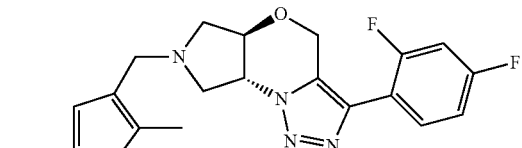 | 2.13 |
| Example 26 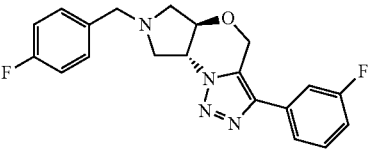 [SMILES: Fc1ccc(CN2C[C@@H]3[C@@H](C2)OCc2c(-c4cccc(F)c4)nnn23)cc1] ·HCl | >10.00 | 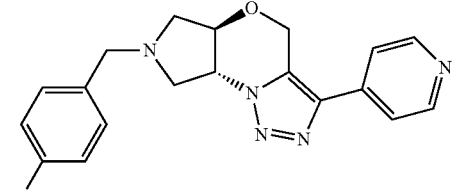 | 3.4 |

-continued
| Compound of the present invention | Kin. Solub. (μM) | Compound of WO2009071657 | Kin. Solub. (μM) |
|---|---|---|---|
| Example 44 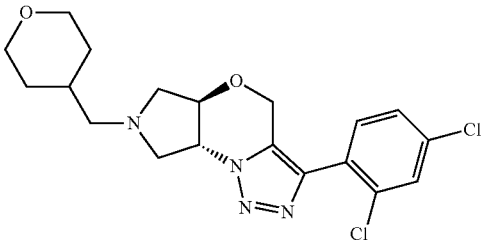 •HCl | >10.00 | 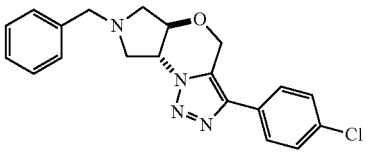 | 0.93 |
| Example 54 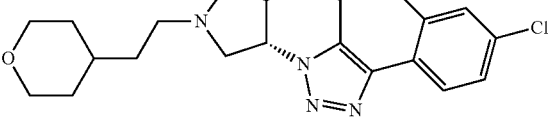 •HCl | >10.00 | 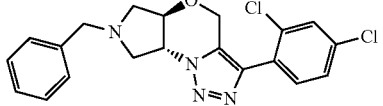 | 7.8 |
| Example 55 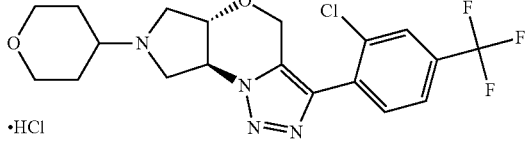 •HCl | >10.00 | 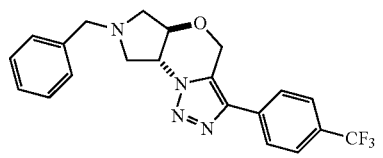 | <0.40 |
| Example 64 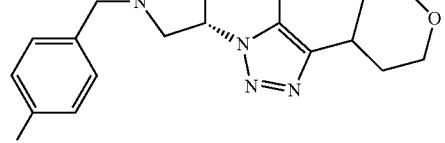 •HCl | >10.00 | 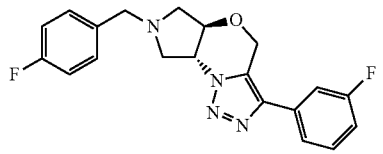 [SMILES: Fc1ccc(CN2C[C@@H]3[C@@H](C2)OCc2c(-c4cccc(F)c4)nnn23)cc1] | 3.9 |
| Example 66 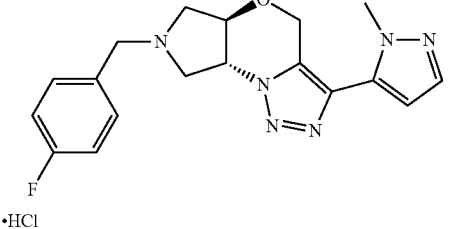 •HCl | >10.00 | | |

-continued
| Compound of the present invention | Kin. Solub. (μM) | Compound of WO2009071657 | Kin. Solub. (μM) |
|---|---|---|---|
| Example 8 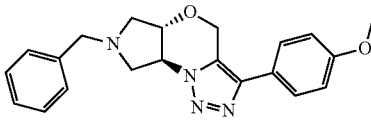 [SMILES: COc1ccc(-c2nnn3c2CO[C@H]2CN(Cc4ccccc4)C[C@@H]23)cc1] •HCl | >10.00 | 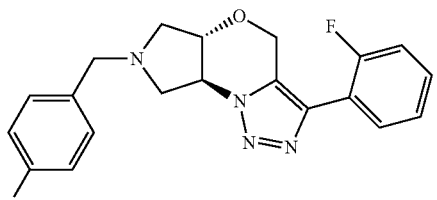 | 2.1 |
| Example 11 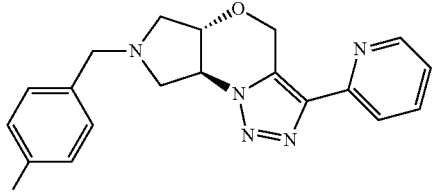 •HCl | >10.00 | 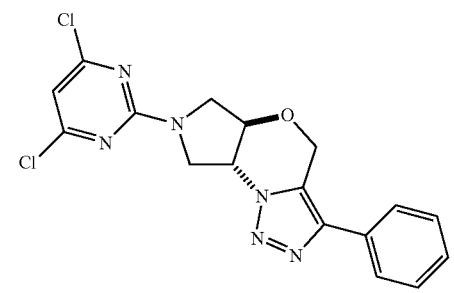 | 3.08 |
| Example 25 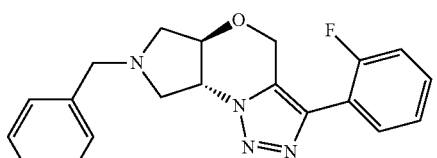 •HCl | >10.00 | | |
Table III represents a comparative example between compound 47 of WO2009/071657 with some of the more structural related compounds of the present invention:
| Compound of WO2009071657 | Kin. Solub. (μM) | Compound of the present invention | Kin. Solub. (μM) |
|---|---|---|---|
| | <1.00 | Example 1 •HCl | >20.00 |

| Compound of WO2009071657 | Kin. Solub. (μM) | Compound of the present invention | Kin. Solub. (μM) |
|---|---|---|---|
| | | Example 2 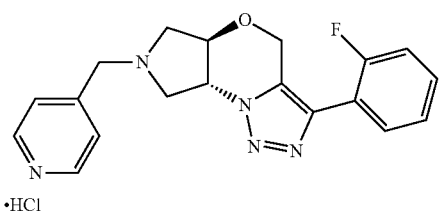 [SMILES: Fc1ccccc1-c1nnn2c1CO[C@@H]1CN(Cc3ccncc3)C[C@H]12 ; Cl] •HCl | >10.00 |
| | | Example 3 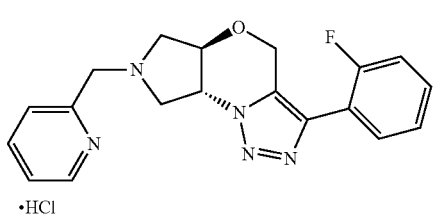 [SMILES: Fc1ccccc1-c1nnn2c1CO[C@@H]1CN(Cc3ccccn3)C[C@H]12 ; Cl] •HCl | >10.00 |
| | | Example 4 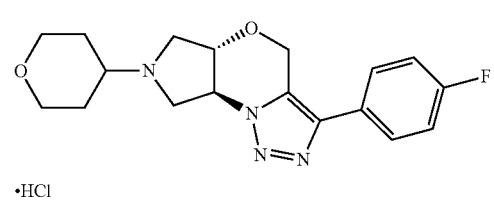 [SMILES: Fc1ccc(-c2nnn3c2CO[C@H]2CN(C4CCOCC4)C[C@@H]23)cc1 ; Cl] •HCl | >10.00 |
| | | Example 5 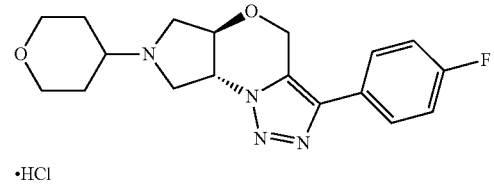 [SMILES: Fc1ccc(-c2nnn3c2CO[C@@H]2CN(C4CCOCC4)C[C@H]23)cc1 ; Cl] •HCl | >10.00 |
| | | Example 6 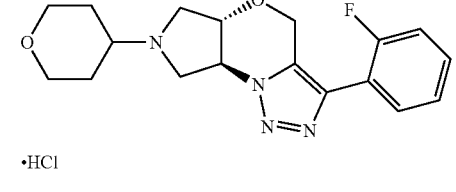 •HCl | >10.00 |
| | | Example 7 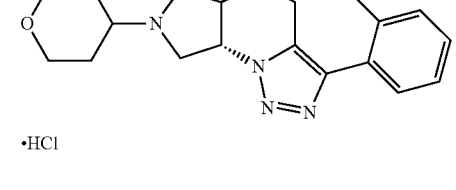 •HCl | >10.00 |

| Compound of WO2009071657 | Kin. Solub. (μM) | Compound of the present invention | Kin. Solub. (μM) |
|---|---|---|---|
| | | Example 11 | >10.00 |
| | | Example 39 | |

As observed in comparative table II and table III, although compounds of WO2009/071657 are structurally related to the compounds of the present invention, the latter have a clearly improved solubility when compared to those of the prior art.

In addition, it should be stressed that some of the compounds of WO2009/071657 with heteroaryl groups attached to the nitrogen of the pyrrolidine of the tricyclic structure such as compounds 48, 51 and 52 of WO2009/071657, were not soluble in DMSO which in practice makes them practically useless from the pharmacological point of view. On the contrary, all compounds of the present invention have a good solubility in DMSO.

Biological Activity
Pharmacological Study
Human Sigma 1 Receptor Radioligand Assay To investigate binding properties of sigma 1 receptor ligands to human sigma 1 receptor, transfected HEK-293 membranes and [$^3$H](+)-pentazocine (Perkin Elmer, NET-1056), as the radioligand, were used. The assay was carried out with 7 μg of membrane suspension, 5 nM of [$^3$H](+)-pentazocine in either absence or presence of either buffer or 10 μM Haloperidol for total and non-specific binding, respectively. Binding buffer contained Tris-HCl 50 mM at pH 8. Plates were incubated at 37° C. for 120 minutes. After the incubation period, the reaction mix was then transferred to MultiScreen HTS, FC plates (Millipore), filtered and plates were washed 3 times with ice-cold 10 mM Tris-HCL (pH7.4). Filters were dried and counted at approximately 40% efficiency in a MicroBeta scintillation counter (Perkin-Elmer) using EcoScint liquid scintillation cocktail.

Some of the results obtained are shown in table III.

TABLE III

| EX | $K_i$ (nM) |
|---|---|
| 1 | 122 |
| 2 | 315.5 |

TABLE III-continued

| EX | $K_i$ (nM) |
|---|---|
| 4 | 23 |
| 6 | 21.6 |
| 7 | 209.1 |
| 8 | 227.2 |
| 9 | 16.1 |
| 10 | 13.9 |
| 11 | 240.7 |
| 12 | 51.5 |
| 13 | 391.8 |
| 14 | 86.9 |
| 15 | 29.7 |
| 16 | 97.6 |
| 17 | 49.2 |
| 18 | 171.2 |
| 19 | 83.3 |
| 21 | 16.6 |
| 22 | 118.6 |
| 23 | 41.9 |
| 24 | 21 |
| 26 | 133.2 |
| 27 | 20.4 |
| 29 | 119 |
| 30 | 63.4 |
| 31 | 241.5 |
| 32 | 37 |
| 33 | 224.6 |
| 35 | 85.7 |
| 36 | 74.2 |
| 38 | 21.8 |
| 39 | 165.5 |
| 40 | 25.9 |
| 41 | 19.9 |
| 42 | 33.3 |
| 43 | 20.5 |
| 44 | 30.8 |
| 45 | 13.7 |
| 46 | 15.1 |
| 47 | 26.8 |
| 48 | 11.7 |
| 49 | 111.6 |

TABLE III-continued

| EX | $K_i$ (nM) |
|---|---|
| 50 | 99.9 |
| 51 | 233.8 |
| 52 | 271.9 |
| 53 | 16.8 |
| 54 | 71.4 |
| 55 | 23.3 |
| 56 | 22.7 |
| 57 | 195.4 |
| 58 | 25.4 |
| 59 | 180.5 |
| 60 | 101.9 |
| 61 | 73.7 |
| 62 | 39.2 |
| 63 | 37.7 |
| 64 | 71.8 |
| 66 | 138.1 |

The invention claimed is:

1. A compound of formula (I)

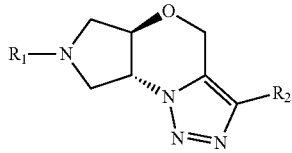

wherein
R$_1$ is selected from:
  a —(C(R$_3$)$_2$)$_m$-aryl group in which the aryl group may be optionally substituted by at least one halogen atom;
  a —(C(R$_3$)$_2$)$_m$-heteroaryl group in which the heteroaryl group may be optionally substituted by at least one substituent selected from a halogen, C$_{1-3}$-alkyl, C$_{1-3}$-alkoxy, C$_{1-3}$-haloalcoxy or C$_{1-3}$-haloalkyl and in which the heteroaryl group may optionally be condensed with an additional ring system;
  a —(C(R$_3$)$_2$)$_n$-heterocycloalkyl group, in which the heterocycloalkyl may be optionally substituted by at least one substituent selected from a halogen, C$_{1-3}$-alkyl, C$_{1-3}$-alkoxy, C$_{1-3}$-haloalcoxy or C$_{1-3}$-haloalkyl and contains at least one oxygen atom;
R$_2$ is selected from:
  a phenyl group optionally substituted by at least one substitutent selected from a halogen, C$_{1-3}$-alkoxy, C$_{1-3}$-haloalcoxy, C$_{1-3}$-haloalkyl or a hydroxyl group;
  a heteroaryl group optionally substituted by at least one substitutent selected from a halogen, C$_{1-3}$-alkyl C$_{1-3}$-alkoxy, C$_{1-3}$haloalcoxy, C$_{1-3}$-haloalkyl or a hydroxyl group;
  a heterocycloalkyl group and being optionally substituted by at least one substituent selected from a halogen, C$_{1-3}$-alkyl, C$_{1-3}$-alkoxy, C$_{1-3}$-haloalcoxy, C$_{1-3}$-haloalkyl or a hydroxyl group;
R$_3$ is H or C$_{1-3}$ alkyl;
m is 1 to 3; and
n is 0 to 3;
with the proviso that when R$_1$ is a —(C(R$_3$)$_2$)$_m$-aryl group, R$_2$ is not a phenyl group;
or a pharmaceutically acceptable salt, isomer, prodrug or solvate thereof.

2. A compound according to claim 1, wherein R$_1$ is a benzyl optionally substituted by at least one halogen; a —(C(R$_3$)$_2$)$_m$-heteroaryl group in which the heteroaryl is a 5 or 6 membered heteroaryl radical containing from 1 to 3 heteroatoms selected from N or O and is optionally substituted by at least one substituent selected from a halogen, C$_{1-3}$-alkyl, C$_{1-3}$-alkoxy or C$_{1-3}$-haloalkyl; or a —(C(R$_3$)$_2$)$_n$-heterocycloalkyl group, in which the heterocycloalkyl group is a tetrahydropyranyl or as tetrahydrofuranyl group.

3. A compound according to claim 1, wherein R$_1$ is selected from:

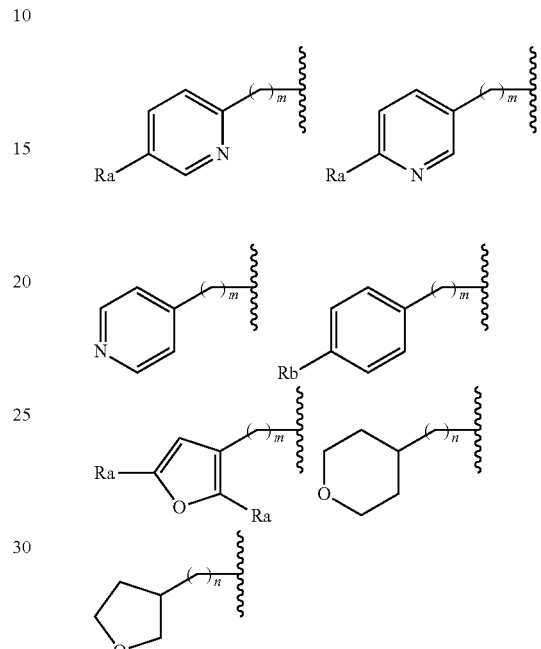

wherein R$_a$ represents a hydrogen, a halogen, C$_{1-3}$ alkyl, C$_{1-3}$-alkoxy or C$_{1-3}$ haloalkyl, R$_b$ represents a hydrogen or a halogen and m and n are as defined in claim 1.

4. A compound according to claim 1, wherein R$_2$ is a phenyl optionally substituted by at least one substituent selected from a halogen or C$_{1-3}$ haloalkyl; a 5 or 6 membered heteroaryl radical containing from 1 to 3 N atoms and optionally substituted by at least one substituent selected from a halogen, C$_{1-3}$-alkyl or C$_{1-3}$-alkoxy; or a tetrahydropyranyl group.

5. A compound according to claim 1, wherein R$_2$ is selected from:

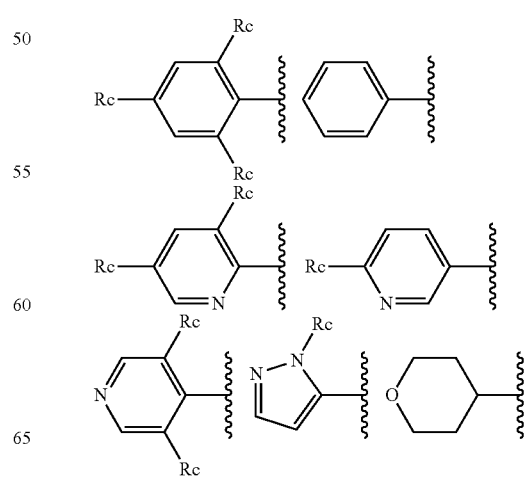

wherein represents a hydrogen, halogen, $C_{1-3}$ alkyl, $C_{1-3}$ alkoxy, $C_{1-3}$ haloalkyl.

6. A compound according to claim 1, wherein $R_1$ is selected from:

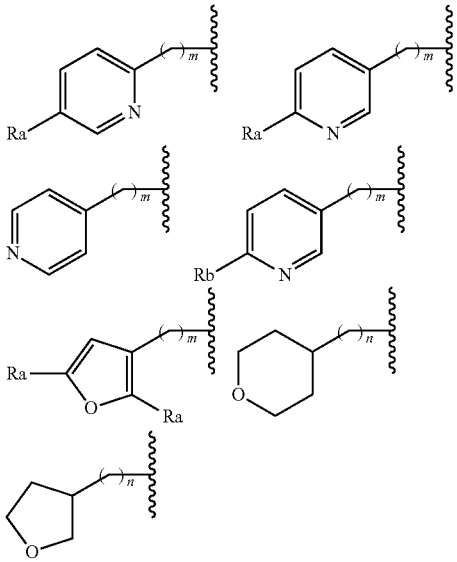

$R_2$ is selected from:

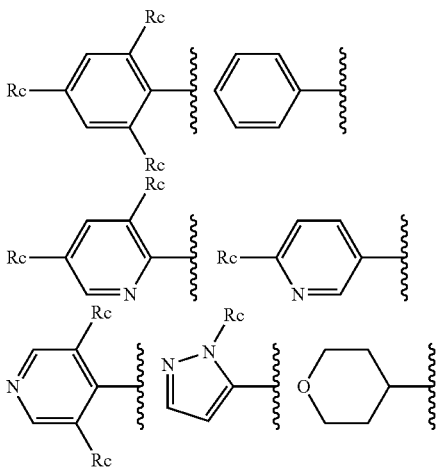

wherein $R_a$ represents a hydrogen, a halogen, $C_{1-3}$ alkyl, $C_{1-3}$-alkoxy or $C_{1-3}$ haloalkyl, $R_b$ represents a hydrogen or a halogen, $R_c$ represents a hydrogen, halogen, $C_{1-3}$ alkyl, $C_{1-3}$ alkoxy, $C_{1-3}$ haloalkyl and m and n are as defined in claim 1.

7. A compound according to claim 1, selected from the group consisting of:
- (5aR,8aR)-3-(2-fluorophenyl)-7-(pyridin-3-ylmethyl)-4,5a,6,7,8,8a-hexahydropyrrolo[3,4-b][1,2,3]triazolo[1,5-d][1,4]oxazine hydrochloride
- (5aRS,8aRS)-3-(2-fluorophenyl)-7-(pyridin-4-ylmethyl)-4,5a,6,7,8,8a-hexahydropyrrolo[3,4-b][1,2,3]triazolo[1,5-d][1,4]oxazine hydrochloride
- (5aRS,8aRS)-3-(2-fluorophenyl)-7-(pyridin-2-ylmethyl)-4,5a,6,7,8,8a-hexahydropyrrolo[3,4-b][1,2,3]triazolo[1,5-d][1,4]oxazine hydrochloride
- (5aS,8aS)-3-(4-fluorophenyl)-7-(tetrahydro-2H-pyran-4-yl)-4,5a,6,7,8,8a-hexahydropyrrolo[3,4-b][1,2,3]triazolo[1,5-d][1,4]oxazine hydrochloride
- (5aR,8aR)-3-(4-fluorophenyl)-7-(tetrahydro-2H-pyran-4-yl)-4,5a,6,7,8,8a-hexahydropyrrolo[3,4-b][1,2,3]triazolo[1,5-d][1,4]oxazine hydrochloride
- (5aS,8aS)-3-(2-fluorophenyl)-7-(tetrahydro-2H-pyran-4-yl)-4,5a,6,7,8,8a-hexahydropyrrolo[3,4-b][1,2,3]triazolo[1,5-d][1,4]oxazine hydrochloride
- (5aR,8aR)-3-(2-fluorophenyl)-7-(tetrahydro-2H-pyran-4-yl)-4,5a,6,7,8,8a-hexahydropyrrolo[3,4-b][1,2,3]triazolo[1,5-d][1,4]oxazine hydrochloride
- (5aS,8aS)-3-(6-methoxypyridin-3-yl)-7-(tetrahydro-2H-pyran-4-yl)-4,5a,6,7,8,8a-hexahydropyrrolo[3,4-b][1,2,3]triazolo[1,5-d][1,4]oxazine hydrochloride
- (5aS,8aS)-3-(2-fluorophenyl)-7-((tetrahydro-2H-pyran-4-yl)methyl)-4,5a,6,7,8,8a-hexahydropyrrolo[3,4-b][1,2,3]triazolo[1,5-d][1,4]oxazine hydrochloride
- (5aR,8aR)-3-(2-fluorophenyl)-7-((tetrahydro-2H-pyran-4-yl)methyl)-4,5a,6,7,8,8a-hexahydropyrrolo[3,4-b][1,2,3]triazolo[1,5-d][1,4]oxazine hydrochloride
- (5aR,8aR)-3-(2-fluorophenyl)-7-((6-fluoropyridin-3-yl)methyl)-4,5a,6,7,8,8a-hexahydropyrrolo[3,4-b][1,2,3]triazolo[1,5-d][1,4]oxazine hydrochloride
- (5aR,8aR)-3-(2-fluorophenyl)-7-((6-methoxypyridin-3-yl)methyl)-4,5a,6,7,8,8a-hexahydropyrrolo[3,4-b][1,2,3]triazolo[1,5-d][1,4]oxazine hydrochloride
- (5aS,8aS)-3-(2-fluorophenyl)-7-((6-methoxypyridin-3-yl)methyl)-4,5a,6,7,8,8a-hexahydropyrrolo[3,4-b][1,2,3]triazolo[1,5-d][1,4]oxazine hydrochloride
- (5aR,8aR)-3-(2-fluorophenyl)-7-((6-(trifluoromethyl)pyridin-3-yl)methyl)-4,5a,6,7,8,8a-hexahydropyrrolo[3,4-b][1,2,3]triazolo[1,5-d][1,4]oxazine hydrochloride
- (5aS,8aS)-3-(2-fluorophenyl)-7-(((R)-tetrahydrofuran-3-yl)methyl)-4,5a,6,7,8,8a-hexahydropyrrolo[3,4-b][1,2,3]triazolo[1,5-d][1,4]oxazine hydrochloride
- (5aR,8aR)-3-(2-fluorophenyl)-7-(((S)-tetrahydrofuran-3-yl)methyl)-4,5a,6,7,8,8a-hexahydropyrrolo[3,4-b][1,2,3]triazolo[1,5-d][1,4]oxazine hydrochloride
- (5aS,8aS)-3-(2-fluorophenyl)-7-(((S)-tetrahydrofuran-3-yl)methyl)-4,5a,6,7,8,8a-hexahydropyrrolo[3,4-b][1,2,3]triazolo[1,5-d][1,4]oxazine hydrochloride
- (5aR,8aR)-3-(2-fluorophenyl)-7-(((R)-tetrahydrofuran-3-yl)methyl)-4,5a,6,7,8,8a-hexahydropyrrolo[3,4-b][1,2,3]triazolo[1,5-d][1,4]oxazine hydrochloride
- (5aR,8aR)-7-((6-ethoxypyridin-3-yl)methyl)-3-(2-fluorophenyl)-4,5a,6,7,8,8a-hexahydropyrrolo[3,4-b][1,2,3]triazolo[1,5-d][1,4]oxazine hydrochloride
- (5aS,8aS)-7-((6-ethoxypyridin-3-yl)methyl)-3-(2-fluorophenyl)-4,5a,6,7,8,8a-hexahydropyrrolo[3,4-b][1,2,3]triazolo[1,5-d][1,4]oxazine hydrochloride
- (5aRS,8aRS)-3-(4-fluorophenyl)-7-(furan-3-ylmethyl)-4,5a,6,7,8,8a-hexahydropyrrolo[3,4-b][1,2,3]triazolo[1,5-d][1,4]oxazine hydrochloride
- (5aS,8aS)-3-(2,4-difluorophenyl)-7-((2,5-dimethylfuran-3-yl)methyl)-4,5a,6,7,8,8a-hexahydropyrrolo[3,4-b][1,2,3]triazolo[1,5-d][1,4]oxazine hydrochloride
- (5aR,8aR)-3-(2,4-difluorophenyl)-7-((2,5-dimethylfuran-3-yl)methyl)-4,5a,6,7,8,8a-hexahydropyrrolo[3,4-b][1,2,3]triazolo[1,5-d][1,4]oxazine hydrochloride
- (5aR,8aR)-7-(4-fluorobenzyl)-3-(pyridin-2-yl)-4,5a,6,7,8,8a-hexahydropyrrolo[3,4-b][1,2,3]triazolo[1,5-d][1,4]oxazine hydrochloride
- (5aS,8aS)-7-(4-fluorobenzyl)-3-(pyridin-2-yl)-4,5a,6,7,8,8a-hexahydropyrrolo[3,4-b][1,2,3]triazolo[1,5-d][1,4]oxazine hydrochloride (5aRS,8aRS)-7-(4-fluorobenzyl)-3-(pyridin-4-yl)-4,5a,6,7,8,8a-hexahydropyrrolo[3,4-b][1,2,3]triazolo[1,5-d][1,4]oxazine hydrochloride
(5aS,8aS)-3-(2,4-difluorophenyl)-7-(tetrahydro-2H-pyran-4-yl)-4,5a,6,7,8,8a-hexahydropyrrolo[3,4-b][1,2,3]triazolo[1,5-d][1,4]oxazine hydrochloride
(5aR,8aR)-3-(2,4-difluorophenyl)-7-(tetrahydro-2H-pyran-4-yl)-4,5a,6,7,8,8a-hexahydropyrrolo[3,4-b][1,2,3]triazolo[1,5-d][1,4]oxazine hydrochloride
(5aR,8aR)-7-(4-fluorobenzyl)-3-(3-fluoropyridin-2-yl)-4,5a,6,7,8,8a-hexahydropyrrolo[3,4-b][1,2,3]triazolo[1,5-d][1,4]oxazine hydrochloride
(5aS,8aS)-3-(5-fluoropyridin-2-yl)-7-(tetrahydro-2H-pyran-4-yl)-4,5a,6,7,8,8a-hexahydropyrrolo[3,4-b][1,2,3]triazolo[1,5-d][1,4]oxazine hydrochloride
(5aS,8aS)-3-(pyridin-2-yl)-7-(tetrahydro-2H-pyran-4-yl)-4,5a,6,7,8,8a-hexahydropyrrolo[3,4-b][1,2,3]triazolo[1,5-d][1,4]oxazine hydrochloride
(5aR,8aR)-7-benzyl-3-(pyridin-2-yl)-4,5a,6,7,8,8a-hexahydropyrrolo[3,4-b][1,2,3]triazolo[1,5-d][1,4]oxazine hydrochloride
(5aS,8aS)-7-benzyl-3-(pyridin-2-yl)-4,5a,6,7,8,8a-hexahydropyrrolo[3,4-b][1,2,3]triazolo[1,5-d][1,4]oxazine hydrochloride
(5aS,8aS)-7-(4-fluorobenzyl)-3-(pyridin-3-yl)-4,5a,6,7,8,8a-hexahydropyrrolo[3,4-b][1,2,3]triazolo[1,5-d][1,4]oxazine hydrochloride
(5aR,8aR)-7-(4-fluorobenzyl)-3-(pyridin-3-yl)-4,5a,6,7,8,8a-hexahydropyrrolo[3,4-b][1,2,3]triazolo[1,5-d][1,4]oxazine hydrochloride
(5aR,8aR)-7-(4-fluorobenzyl)-3-(3-fluoropyridin-4-yl)-4,5a,6,7,8,8a-hexahydropyrrolo[3,4-b][1,2,3]triazolo[1,5-d][1,4]oxazine hydrochloride
(5aS,8aS)-7-(4-fluorobenzyl)-3-(3-fluoropyridin-4-yl)-4,5a,6,7,8,8a-hexahydropyrrolo[3,4-b][1,2,3]triazolo[1,5-d][1,4]oxazine hydrochloride
(5aS,8aS)-3-(2-chloro-4-fluorophenyl)-7-(tetrahydro-2H-pyran-4-yl)-4,5a,6,7,8,8a-hexahydropyrrolo[3,4-b][1,2,3]triazolo[1,5-d][1,4]oxazine hydrochloride
(5aR,8aR)-3-(2-chloro-4-fluorophenyl)-7-((6-fluoropyridin-3-yl)methyl)-4,5a,6,7,8,8a-hexahydropyrrolo[3,4-b][1,2,3]triazolo[1,5-d][1,4]oxazine hydrochloride
(5aR,8aR)-3-(2,4-difluorophenyl)-7-(2-(tetrahydro-2H-pyran-4-yl)ethyl)-4,5a,6,7,8,8a-hexahydropyrrolo[3,4-b][1,2,3]triazolo[1,5-d][1,4]oxazine hydrochloride
(5aS,8aS)-3-(2,4-difluorophenyl)-7-(2-(tetrahydro-2H-pyran-4-yl)ethyl)-4,5a,7,8,8a-hexahydropyrrolo[3,4-b][1,2,3]triazolo[1,5-d][1,4]oxazine hydrochloride
(5aR,8aR)-3-(2-chloro-4-fluorophenyl)-7-((tetrahydro-2H-pyran-4-yl)methyl)-4,5a,6,7,8,8a-hexahydropyrrolo[3,4-b][1,2,3]triazolo[1,5-d][1,4]oxazine hydrochloride
(5aS,8aS)-3-(2-chloro-4-fluorophenyl)-7-((tetrahydro-2H-pyran-4-yl)methyl)-4,5a,6,7,8,8a-hexahydropyrrolo[3,4-b][1,2,3]triazolo[1,5-d][1,4]oxazine hydrochloride
(5aR,8aR)-3-(2,4-dichlorophenyl)-7-((tetrahydro-2H-pyran-4-yl)methyl)-4,5a,6,7,8,8a-hexahydropyrrolo[3,4-b][1,2,3]triazolo[1,5-d][1,4]oxazine hydrochloride
(5aS,8aS)-3-(2,4-dichlorophenyl)-7-((tetrahydro-2H-pyran-4-yl)methyl)-4,5a,6,7,8,8a-hexahydropyrrolo[3,4-b][1,2,3]triazolo[1,5-d][1,4]oxazine hydrochloride
(5aS,8aS)-3-(2,4-dichlorophenyl)-7-(tetrahydro-2H-pyran-4-yl)-4,5a,6,7,8,8a-hexahydropyrrolo[3,4-b][1,2,3]triazolo[1,5-d][1,4]oxazine hydrochloride
(5aR,8aR)-3-(2-chloro-4-fluorophenyl)-7-(2-(tetrahydro-2H-pyran-4-yl)ethyl)-4,5a,6,7,8,8a-hexahydropyrrolo[3,4-b][1,2,3]triazolo[1,5-d][1,4]oxazine hydrochloride
(5aS,8aS)-3-(2-chloro-4-fluorophenyl)-7-(2-(tetrahydro-2H-pyran-4-yl)ethyl)-4,5a,6,7,8,8a-hexahydropyrrolo[3,4-b][1,2,3]triazolo[1,5-d][1,4]oxazine hydrochloride
(5aR,8aR)-3-(2-chloro-4-fluorophenyl)-7-((6-methoxypyridin-3-yl)methyl)-4,5a,6,7,8,8a-hexahydropyrrolo[3,4-b][1,2,3]triazolo[1,5-d][1,4]oxazine hydrochloride
(5aS,8aS)-3-(2-chloro-4-fluorophenyl)-7-((6-methoxypyridin-3-yl)methyl)-4,5a,6,7,8,8a-hexahydropyrrolo[3,4-b][1,2,3]triazolo[1,5-d][1,4]oxazine hydrochloride
(5aR,8aR)-3-(2,4-difluorophenyl)-7-((6-methoxypyridin-3-yl)methyl)-4,5a,6,7,8,8a-hexahydropyrrolo[3,4-b][1,2,3]triazolo[1,5-d][1,4]oxazine hydrochloride
(5aS,8aS)-3-(2,4-difluorophenyl)-7-((6-methoxypyridin-3-yl)methyl)-4,5a,6,7,8,8a-hexahydropyrrolo[3,4-b][1,2,3]triazolo[1,5-d][1,4]oxazine hydrochloride
(5aS,8aS)-3-(2,4-dichlorophenyl)-7-(2-(tetrahydro-2H-pyran-4-yl)ethyl)-4,5a,6,7,8,8a-hexahydropyrrolo[3,4-b][1,2,3]triazolo[1,5-d][1,4]oxazine hydrochloride
(5aR,8aR)-3-(2,4-dichlorophenyl)-7-(2-(tetrahydro-2H-pyran-4-yl)ethyl)-4,5a,6,7,8,8a-hexahydropyrrolo[3,4-b][1,2,3]triazolo[1,5-d][1,4]oxazine hydrochloride
(5aS,8aS)-3-(2-chloro-4-(trifluoromethyl)phenyl)-7-(tetrahydro-2H-pyran-4-yl)-4,5a,6,7,8,8a-hexahydropyrrolo[3,4-b][1,2,3]triazolo[1,5-d][1,4]oxazine hydrochloride
(5aS,8aS)-3-(2,4-dichlorophenyl)-7-(((S)-tetrahydrofuran-3-yl)methyl)-4,5a,6,7,8,8a-hexahydropyrrolo[3,4-b][1,2,3]triazolo[1,5-d][1,4]oxazine hydrochloride
(5aR,8aR)-3-(2,4-dichlorophenyl)-7-(((R)-tetrahydrofuran-3-yl)methyl)-4,5a,6,7,8,8a-hexahydropyrrolo[3,4-b][1,2,3]triazolo[1,5-d][1,4]oxazine hydrochloride
(5aS,8aS)-3-(2,4-dichlorophenyl)-7-(((R)-tetrahydrofuran-3-yl)methyl)-4,5a,6,7,8,8a-hexahydropyrrolo[3,4-b][1,2,3]triazolo[1,5-d][1,4]oxazine hydrochloride
(5aR,8aR)-3-(2,4-dichlorophenyl)-7-(((S)-tetrahydrofuran-3-yl)methyl)-4,5a,6,7,8,8a-hexahydropyrrolo[3,4-b][1,2,3]triazolo[1,5-d][1,4]oxazine hydrochloride
(5aR,8aR)-3-(2,4-difluorophenyl)-7-((2-methylfuran-3-yl)methyl)-4,5a,6,7,8,8a-hexahydropyrrolo[3,4-b][1,2,3]triazolo[1,5-d][1,4]oxazine hydrochloride
(5aS,8aS)-3-(2,4-difluorophenyl)-7-((2-methylfuran-3-yl)methyl)-4,5a,6,7,8,8a-hexahydropyrrolo[3,4-b][1,2,3]triazolo[1,5-d][1,4]oxazine hydrochloride
(5aS,8aS)-3-(2,4-difluorophenyl)-7-(furan-3-ylmethyl)-4,5a,6,7,8,8a-hexahydropyrrolo[3,4-b][1,2,3]triazolo[1,5-d][1,4]oxazine hydrochloride
(5aR,8aR)-3-(2,4-difluorophenyl)-7-(furan-3-ylmethyl)-4,5a,6,7,8,8a-hexahydropyrrolo[3,4-b][1,2,3]triazolo[1,5-d][1,4]oxazine hydrochloride
(5aR,8aR)-7-(4-fluorobenzyl)-3-(tetrahydro-2H-pyran-4-yl)-4,5a,6,7,8,8a-hexahydropyrrolo[3,4-b][1,2,3]triazolo[1,5-d][1,4]oxazine hydrochloride
(5aS,8aS)-7-(4-fluorobenzyl)-3-(tetrahydro-2H-pyran-4-yl)-4,5a,6,7,8,8a-hexahydropyrrolo[3,4-b][1,2,3]triazolo[1,5-d][1,4]oxazine hydrochloride
(5aR,8aR)-7-(4-fluorobenzyl)-3-(1-methyl-1H-pyrazol-5-yl)-4,5a,6,7,8,8a-hexahydropyrrolo[3,4-b][1,2,3]triazolo[1,5-d][1,2,3]oxazine hydrochloride, and
pharmaceutically acceptable salts, solvates and prodrugs thereof.

8. A method of treatment and/or prophylaxis of a patient suffering from a sigma receptor mediated disease or condition selected from the group consisting of pain, diarrhea, lipoprotein disorders, hyperlipidemia, hypertriglyceridemia, hypercholesterolemia, obesity, migraine, arthritis, hypertension, arrhythmia, ulcer, glaucoma, learning, memory and attention deficits, demyelinating diseases, addiction to drugs and chemical substances, tardive dyskinesia, ischemic stroke, epilepsy, stroke, and stress, the method comprising administering to the patient in need of such a treatment a therapeutically effective amount of a compound of claim 1 or a pharmaceutically acceptable salt, isomer, prodrug or solvate thereof.

9. The method of claim 8, wherein the disease or condition is pain.

10. The method of claim 8, wherein the disease or condition is selected from the group consisting of addiction to cocaine, addiction to amphetamine, addiction to ethanol and addiction to nicotine.

11. A process for the preparation of a compound of formula (Ia):

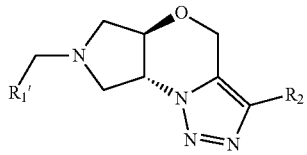

comprising a reaction between a compound of general formula (VI):

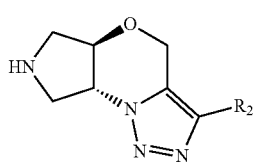

with an aldehyde of general formula (VII):

wherein $R_2$ is as defined in claim 1 and $R_1'$ is selected from is selected from:

a —$(C(R_3)_2)_m$-aryl group in which the aryl group may be optionally substituted by at least one halogen atom;

a —$(C(R_3)_2)_m$-heteroaryl group in which the heteroaryl group may be optionally substituted by at least one substituent selected from a halogen, $C_{1-3}$-alkyl, $C_{1-3}$-alkoxy, $C_{1-3}$-haloalkoxy or $C_{1-3}$-haloalkyl and in which the heteroaryl group may optionally be condensed with an additional ring system;

a —$(C(R_3)_2)_n$-heterocycloalkyl group, in which the heterocycloalkyl group may be optionally substituted by at least one substituent selected from a halogen, $C_{1-3}$-alkyl, $C_{1-3}$-alkoxy, $C_{1-3}$-haloalkoxy or $C_{1-3}$-haloalkyl and contains at least one oxygen atom;

wherein $R_3$ is H or $C_{1-3}$ alkyl;

m is 1 to 2; and n is 0 to 2;

with the proviso that when $R_1$ is a —$(C(R_3)_2)_m$-aryl group, $R_2$ is not a phenyl group.

12. A process for the preparation of a compound of formula (Ia):

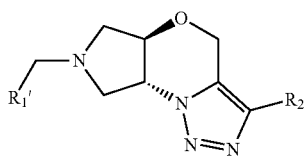

comprising a reduction of a compound of general formula (IX):

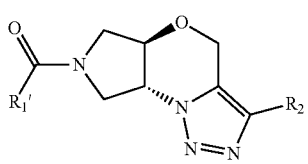

wherein $R_2$ is as defined in claim 1 and $R_1'$ is selected from is selected from:

a —$(C(R_3)_2)_m$-aryl group in which the aryl group may be optionally substituted by at least one halogen atom;

a —$(C(R_3)_2)_m$-heteroaryl group in which the heteroaryl group may be optionally substituted by at least one substituent selected from a halogen, $C_{1-3}$-alkyl, $C_{1-3}$-alkoxy, $C_{1-3}$-haloalkoxy or $C_{1-3}$-haloalkyl and in which the heteroaryl group may optionally be condensed with an additional ring system;

a —$(C(R_3)_2)_n$-heterocycloalkyl group, in which the heterocycloalkyl group may be optionally substituted by at least one substituent selected from a halogen, $C_{1-3}$-alkyl, $C_{1-3}$-alkoxy, $C_{1-3}$-haloalkoxy or $C_{1-3}$-haloalkyl and contains at least one oxygen atom;

being $R_3$ is H or $C_{1-3}$ alkyl;

m is 1 to 2; and n is 0 to 2;

with the proviso that when $R_1$ is a —$(C(R_3)_2)_m$-aryl group, $R_2$ is not a phenyl group.

13. A process for the preparation of a compound of general formula (I):

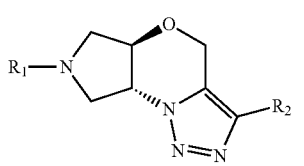

comprising a reaction between a compound of general formula (VI):

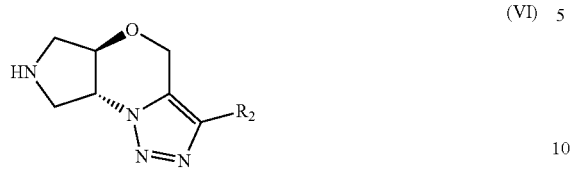

(VI)

with an ketone of general formula (VIIa):

O=R₁   (VIIa)

wherein $R_1$ represents a —$(C(R_3)_2)_n$-heterocycloalkyl group, in which the heterocycloalkyl group may be optionally substituted by at least one substituent selected from a halogen, $C_{1-3}$-alkyl, $C_{1-3}$-alkoxy, $C_{1-3}$-haloalkoxy or $C_{1-3}$-haloalkyl and contains at least one oxygen atom, and n=0.

14. A pharmaceutical composition comprising at least one compound of claim 1, pharmaceutically acceptable salts, prodrugs, isomers or solvates thereof, and at least a pharmaceutically acceptable carrier, additive, adjuvant or vehicle.

15. The method of claim 9, wherein the pain is selected from the group consisting of neuropathic pain, inflammatory pain, and pain conditions involving allodynia and/or hyperalgesia.

* * * * *

UNITED STATES PATENT AND TRADEMARK OFFICE
CERTIFICATE OF CORRECTION

PATENT NO. : 9,512,142 B2
APPLICATION NO. : 14/785128
DATED : December 6, 2016
INVENTOR(S) : José-Luis Díaz-Fernández, Carmen Almansa-Rosales and Félix Cuevas-Cordobés It is certified that error appears in the above-identified patent and that said Letters Patent is hereby corrected as shown below:

On the Title Page

Other publications, Oliva, et al.: "No. 6" should be -- No. 8 --.

Other publications, Quirionx, et al.: "1982" should be -- 1992 --.

In the Claims

Column 63, Line 1: "wherein" should be -- wherein Rc --.

Column 67, Line 1: "and/or prophylaxis" should be deleted.

Column 68, Line 57: "general" should be deleted.

Signed and Sealed this
Eighth Day of May, 2018

Andrei Iancu
*Director of the United States Patent and Trademark Office*